US007541172B2

(12) United States Patent
Wallaart et al.

(10) Patent No.: US 7,541,172 B2
(45) Date of Patent: *Jun. 2, 2009

(54) TRANSGENIC AMORPHA-4, 11-DIENE SYNTHESIS

(75) Inventors: Thorvald Eelco Wallaart, Groningen (NL); Hendrik Jan Bouwmeester, Renkum (NL)

(73) Assignee: Institute for OneWorld Health, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/488,906

(22) Filed: Jul. 18, 2006

(65) Prior Publication Data

US 2007/0031947 A1   Feb. 8, 2007

Related U.S. Application Data

(62) Division of application No. 09/763,822, filed as application No. PCT/EP99/06302 on Aug. 27, 1999, now Pat. No. 7,091,027.

(30) Foreign Application Priority Data

Aug. 27, 1998   (EP)   .................................. 98202854

(51) Int. Cl.
*C07H 21/04* (2006.01)
*C12N 1/20* (2006.01)
*C12N 15/00* (2006.01)

(52) U.S. Cl. .................. 435/232; 435/252.3; 435/320.1; 536/23.2

(58) Field of Classification Search .................. 435/232, 435/193, 252.3, 320.1; 536/23.2
See application file for complete search history.

(56) References Cited

U.S. PATENT DOCUMENTS

| | | | |
|---|---|---|---|
| 6,342,380 B1 * | 1/2002 | Colby et al. | ................. 435/183 |
| 6,495,354 B2 | 12/2002 | Chappell et al. | |
| 7,091,027 B1 * | 8/2006 | Wallaart et al. | ............. 435/232 |

OTHER PUBLICATIONS

Attwood et al. [Comput. Chem. 2001, col. 54(4), pp. 329-39].*
Ponting [Brief. Bioinform. Mar. 2001, vol. 2(1), pp. 19-29].*
Accession No. AF327526 (Liu et al., 2001).*
Guo et al. (PNAS 101(25):9205-9210, 2004).*
Attwood et al., "Which craft is best in bioinformatics?," Computers & Chemistry, 25(4): 329-339 (2001).
Back et al., "Cloning and bacterial expression of a sesquiterpene cyclase from *Hyoscyamus muticus* and its molecular comparison to related terpene cyclases," J. Biol. Chem., 270(13):7375-7381 (1995).
Back et al., "Expression of a plant sesquiterpene cyclase gene in *Escherichia coli*," Archives of Biochemistry and Biophysics, 315(2): 527-532 (1994).

Back et al., "Identifying functional domains within terpene cyclases using a domain-swapping strategy," Proc. Natl. Acad. Sci. USA, 93: 6841-6845 (1996).
Bohlmann et al., "Cadina-4,11-diene from *Viguiera oblongifolia*," Phytochemistry, 23(5): 1183-1184 (1984).
Brodelius et al., "Metabolic engineering of plant secondary metabolism: a tool to improve the productivity of plant cell cultures?," Abstract Papers of the American Chemical Society, p. AGFD026, abstract (1997).
Brodelius, "Metabolic engineering of secondary metabolism in *Vanilla planifolia* and *Artemisia annua*," Book of Abstracts, 211th ACS National Meeting, abstract (Mar. 24-28, 1996).
Chang et al., "Improvement of heterologous protein prouctivity using recombinant *Yarrowia lipolytica* and cyclic fed-batch process strategy," Biotechnology and Bioengineering, 59(3): 379-385 (1998).
Chen et al., "One-step transformation of the dimorphic yeast *Yarrowia lipolytica*," Appl. Microbiol. Biotechnol., 48: 232-235 (1997).
Facchini et al., "Gene family for an elicitor-induced sesquiterpene cyclase in tobacco," Proc. Natl. Acad. Sci. USA., 89: 11088-11092 (1992).
Hohn et al., "Expression of a fungal sesquiterpene cyclase gene in transgenic tobacco," Plant Physiol., 97: 460-462 (1991).
Koepp et al., "Cyclization of geranylgeranyl diphosphate to taxa-4(5),11(12)-diene is the committed step of taxol biosynthesis in pacific yew," J. Biol. Chem., 270(15): 8686-8690 (1995).
Matsushita et al., "Cloning and analysis of a cDNA encoding farnesyl diphosphate synthase from *Artemisia annua*," Gene, 172(2): 207-209 (1996).
Müller et al., "Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from *Yarrowia lipolytics*," Yeast, 14: 1267-1283 (1998).
Omirulleh et al., "Activity of a chimeric promoter with the doubled CaMV 35S enhancer element in protoplast-derived cells and transgenic plants in maize," Plant Molecular Biology, 21: 415-428 (1993).
Park et al., "Expression, secretion, and processing of rice α-amylase in the yeast *Yarrowia lipolytica*," Journal of Biological Chemistry, 272(11): 6876-6881 (1997).
Ponting, "Issues in predicting protein function from sequence," Briefings in Bioinformatics, 2(1): 19-29 (2001).
Rogers et al., "Gene transfer in plants: production of transformed plants using Ti plasmid vectors," Methods in Enzymology, 118: 627-640 (1986).
Sequence alignment between Accession No. AF327526 (Liu et al., "Cloning of sesquiterpene cyclase gene from *Artemisia annua*," submitted Dec. 2001 to the EMBL, GenBank, and DDBJ databases) and Applicants' SEQ ID No. 13, 2001.

(Continued)

*Primary Examiner*—Tekchand Saidha
(74) *Attorney, Agent, or Firm*—Finnegan, Henderson, Farabow, Garrett & Dunner L.L.P.

(57) ABSTRACT

The present invention relates to an isolated DNA sequence encoding a polypeptide having the biological activity of amorpha-4,11-diene synthase. This DNA sequence can be used for the transformation of bacteria, yeasts and plants for the production of amorpha-4,11-diene, a specific precursor in the synthesis of artemisinin, in the respective organisms. The invention also relates to these organisms.

30 Claims, 18 Drawing Sheets

OTHER PUBLICATIONS

Figure 1:
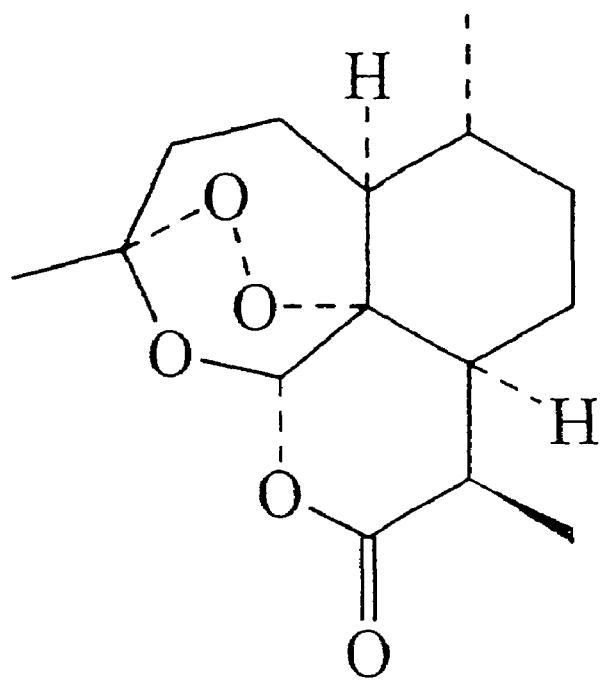

Shimada et al., "Increased carotenoid production by the food yeast *Candida utilis* through metabolic engineering of the Isoprenoid Pathway," Applied and Environmental Microbiology, 64(7): 2676-2680 (1998).

Starks et al., "Structural basis for cyclic terpene biosynthesis by tobacco 5-epi-aristolochene synthase," Science, 277: 1815-1820 (1997).

Tharaud et al., "Secretion of human blood coagulation factor XIIIa by the yeast *Yarrowia lipolytica*," Gene, 121: 111-119 (1992).

Van Geldre et al., "State of the art of the production of the antimalarial compound artemisinin in plants," Plant Molecular Biology, 33(2): 199-209 (1997).

Vergauwe et al., "*Agrobacterium tumefaciens*-mediated transformation of *Artemisia annua* L. and regeneration of transgenic plants," Plant Cell Reports, 15(12): 929-933 (1996).

Wallaart et al., "Bioconversion of dihydroarteannuinic acid into the new antimalarial drug artemisinin," Pharmacy World and Science, 16(3): C4, abstract (1994).

Woerdenbag et al., "Progress in the research of artemisinin-related antimalarials: an update," Pharmacy World and Science, 16(4): 169-180 (1994).

Yanisch-Perron et al., "Improved M13 phage cloning vectors and host strains: nucleotide sequences of the M13mp18 and pUC19 Vectors," Gene 33: 103-119 (1985).

Preliminary Amendment filed Feb. 26, 2001, in U.S. Appl. No. 09/763,822, now U.S. Patent 7,091,027.

Sequence Amendment filed Jul. 29, 2002, in U.S. Appl. No. 09/763,822, now U.S. Patent 7,091,027.

Response to Notification of Defective Response and Sequence Amendment filed May 5, 2003, in U.S. Appl. No. 09/763,822, now U.S. Patent 7,091,027.

Restriction Requirement mailed Apr. 22, 2004, in U.S. Appl. No. 09/763,822, now U.S. Patent 7,091,027.

Election with Traverse filed May 25, 2004, in U.S. Appl. No. 09/763,822, now U.S. Patent 7,091,027.

Non-Final Office Action mailed Jun. 18, 2004, in U.S. Appl. No. 09/763,822, now U.S. Patent 7,091,027.

Amendment filed Sep. 20, 2004, in U.S. Appl. No. 09/763,822, now U.S. Patent 7,091,027.

Non-Final Office Action mailed Dec. 1, 2004, in U.S. Appl. No. 09/763,822, now U.S. Patent 7,091,027.

Amendment filed Jun. 1, 2005, in U.S. Appl. No. 09/763,822, now U.S. Patent 7,091,027.

Final Office Action mailed Sep. 30, 2005, in U.S. Appl. No. 09/763,822, now U.S. Patent 7,091,027.

Amendment After Final filed Feb. 24, 2006, in U.S. Appl. No. 09/763,822, now U.S. Patent 7,091,027.

Notice of Allowance and Fee(s) due mailed Mar. 24, 2006, in U.S. Appl. No. 09/763,822, now U.S. Patent 7,091,027.

* cited by examiner

FIG. 8

```
       Primer A
27   gat gag aat ggg aaa ttt aag gaa tcg tta gct aat gat gtt gaa ggt ttg
      D   E   N   G   K   F   K   E   S   L   A   N   D   V   E   G   L 78   ctt gag ttg tac gaa act gca tct atg agg gta cct ggg gag att ata tta
      L   E   L   Y   E   T   A   S   M   R   V   P   G   E   I   I   L 129  gaa gat gct ctt ggt ttt aca cga tct cgt ctt atg aca aaa gat
      E   D   A   L   G   F   T   R   S   R   L   M   T   K   D 180  gct ttt tct aca aac ccc gct cgt ctt agc att atg aca caa cta aag
      A   F   S   T   N   P   A   R   L   S   I   M   T   Q   L   K 231  caa ccc ttt tct agg aaa ccc ggt ctt acc gaa ttt gaa ata caa cgg gca
      Q   P   F   S   R   K   P   G   L   T   E   F   E   I   Q   R   A 282  ttc tat caa caa gat cat tct cag gat ata gcg cag tac att gct aag
      F   Y   Q   Q   D   H   S   Q   D   I   A   Q   Y   I   A   K 333  tta gag ttc aat aat ctt gag aag gac aac ttg cac ctt cag tac att cat
      L   E   F   N   N   L   E   K   D   N   L   H   L   Q   Y   I   H 384  tgc aaa tgg tgg gaa gtt gat atc tgg gga cta gga cct tca ggc tat gag cca
      C   K   W   W   E   V   D   I   W   G   L   G   P   S   G   Y   E   P 435  gat aga cgg gct aga gtt tgc tac ttc ttc aca aaa gct gtt gct ata act
      D   R   R   A   R   V   C   Y   F   F   T   K   A   V   A   I   T 486  cag tat tcc gac gac acc ttc gac gct acg g
      Q   Y   S   D   D   T   F   D   A   T            (SEQ ID NO. 9)
                 Primer B
                                              (SEQ ID NO. 10)

537  ctt ata gac gac acc ttc gac gct acg g
      L   I   D   D   T   F   D   A   T
```

```
                    EcoR I (Not I) Adapter
  1   aattcgcggc cgcgtcgaca aatcatgtca cttacagaag aaaaacctat
        N  S  R    P  R  R    Q  I  M  S   L  T  E   E  K  P
      ← EcoR I      Not I 51   tcgcccatt gccaactttc ctccaagcat ttggggagat cagtttctca
       I  R  P  I   A  N  F   P  P  S   I  W  G  D   Q  F  L 101   tctatcaaaa gcaagtagag caaggggtgg aacagatagt gaatgattta
       I  Y  Q    K  Q  V  E   Q  G  V    E  Q  I    V  N  D  L 151   aaaaaagaag tgcggcaact actaaagaa gctttggata ttcctatgaa
       K  K  E    V  R  Q    L  L  K  E   A  L  D    I  P  M 201   acatgccaat ttgttgaagc tgattgatga aattcaacgc cttggaatac
       K  H  A  N   L  L  K   L  I  D   E  I  Q  R   L  G  I 251   cgtatcactt tgaacgggag attgatcatg cattgcaatg tatttatgaa
       P  Y  H    F  E  R  E   I  D  H   A  L  Q    C  I  Y  E 301   acatatggtg ataactggaa tggtgaccgc tcttccttat ggttccgtct
       T  Y  G    D  N  W    N  G  D  R   S  S  L    W  F  R 351   tatgcgaaag caaggatatt atgttacatg tgatgttttc aataactata
       L  M  R  K   Q  G  Y    Y  V  T   C  D  V  F   N  N  Y 401   aagacaaaaa tggagcgttc aagcaatcgt tagctaatga tgttgaaggt
       K  D  K    N  G  A  F   K  Q  S    L  A  N   D  V  E  G 451   ttgcttgagt tgtacgaagc aacttctatg agggtacctg gggagattat
       L  L  E    L  Y  E    A  T  S  M   R  V  P    G  E  I 501   attagaagat gctcttggtt tacacgatc tcgtcttagc attatgacaa
       I  L  E  D   A  L  G   F  T  R    S  R  L  S    I  M  T 551   aagatgcttt ttctacaaac cccgctcttt ttaccgaaat acaacgggca
       K  D  A    F  S  T  N   P  A  L   F  T  E  I   Q  R  A 601   ctaaagcaac cccttggaa aaggttgcca agaatagagg cggcgcagta
       L  K  Q    P  L  W    K  R  L  P   R  I  E    A  A  Q 651   cattcctttc tatcaacaac aagattctca taacaagact ttacttaaac
       Y  I  P  F   Y  Q  Q   Q  D  S   H  N  K  T   L  L  K 701   ttgctaagtt agagttcaat ttgcttcagt cattgcacaa ggaagagctc
       L  A  K    L  E  F  N   L  L  Q    S  L  H   K  E  E  L 751   agccatgtgt gcaaatggtg gaaagctttc gatatcaaga gaacgcacc
       S  H  V    C  K  W    W  K  A  F   D  I  K    K  N  A 801   ttgtttaaga gatagaattg ttgaatgcta cttttgggga ctaggttcag
       P  C  L  P   D  P  I    V  E  C    Y  F  W  G   L  G  S 851   gctatgagcc acagtattcc cgggctagag ttttcttcac aaaagctgtt
       G  Y  E    P  Q  Y  S   R  A  P   V  F  F  T   K  A  V
```

FIG. 10-1

```
 901   gctgttataa ctcttataga tgacacttat gatgcgtatg gtacttatga
        A  V  I    T  L  I    D  D  T  Y    D  A  Y    G  T  Y 951   agaacttaag atctttactg aagctgttga aaggtggtca attacatgct
        E  E  L  K    I  F  T    E  A  V    E  R  W  S    I  T  C 1001   tagacacact tccagaatac atgaaaccga tatacaaatt attcatggat
        L  D  T    L  P  E  Y    M  K  P    I  Y  K    L  F  M  D 1051   acatacacag aaatggaaga atttcttgca aaggagggaa gaacagatct
        T  Y  T    E  M  E    E  F  L  A    K  E  G    R  T  D 1101   atttaactgc ggcaaagaat ttgtgaaaga gtttgttaga aacctgatgg
        L  F  N  C    G  K  E    F  V  K    E  F  V  R    N  L  M 1151   ttgaagcaaa atgggcaaat gagggacaca taccaaccac tgaagagcat
        V  E  A  K    W  A  N    E  G  H    I  P  T    T  E  E  H 1201   gatccagttg taatcattac tggcggtgct aacctgctta caacaacttg
        D  P  V    V  I  I    T  G  G  A    N  L  L    T  T  T 1251   ttatcttggc atgagtgata tattcacaaa agagtctgtc gaatgggctg
        C  Y  L  G    M  S  D    I  F  T    K  E  S  V    E  W  A 1301   tctctgcacc tcctcttttt agatactcag gtatacttgg tcgacgccta
        V  S  A    P  P  L  F    R  Y  S    G  I  L    G  R  R  L 1351   aatgatctca tgacccacaa ggccgagcaa gaaagaaaac atagttcatc
        N  D  L    M  T  H    K  A  E  Q    E  R  K    H  S  S 1401   gagccttgaa agttatatga aggaatataa tgtcaatgag gagtatgccc
        S  S  L  E    S  Y  M    K  E  Y    N  V  N  E    E  Y  A 1451   aaaccttgat ttacaaggaa gtagaagatg tgtggaaaga tataaaccga
        Q  T  L    I  Y  K  E    V  E  D    V  W  K    D  I  N  R 1501   gagtacctca caactaaaaa cattccaagg ccgttattga tggctgtgat
        E  Y  L    T  T  K    N  I  P  R    P  L  L    M  A  V 1551   ctatttgtgc cagtttcttg aagttcaata tgcaggaaag gataacttca
        I  Y  L  C    Q  F  L    E  V  Q    Y  A  G  K    D  N  F 1601   cacgtatggg agacgaatac aaacatctca taaagtctct actcgtttat
        T  R  M    G  D  E  Y    K  H  L    I  K  S    L  L  V  Y 1651   cctatgagta tatgactacc aatccttcgt gcatagccta tcaattatat
        P  M  S    I  -  L    P  I  L  P    A  -  P    I  N  Y 1701   tgaaagggtt aactatgcac gtctctatgg agagaatttc tcaagctatt
        I  E  R  V    N  Y  A    R  L  Y    G  E  N  F    S  S  Y
```

FIG. 10-2

```
1751   tggtgtttct  tgctggcaat  aataaatcag  acgcataaaa  ttgtattgaa
        L  V  F    L  A  G  N  N  K  S    D  A  -    N  C  I  E 1801   ctatatgccg  atagctattt  aaagttatta  tacaactaaa  atattcaaca
        L  Y  A    D  S  Y    L  K  L  L  Y  N  -    N  I  Q 1851   atggtattat  acttttactt  tgtacaaaag  caaaagtaca  ctactgttat
        Q  W  Y  Y  T  F  T    L  Y  K    S  K  S  T  L  L  L 1901   gtaacatttt  agttctatga  tactttagtt  acgaatcggc  ttatatacat
        C  N  I    L  V  L  -  Y  F  S    Y  E  S    A  Y  I  H 1951   tgatacactt  ttatgcagaa  aaccctagta  aataaaaagt  cgatatcttg
        -  Y  T    F  M  Q    K  T  L  V  N  K  K    S  I  S 2001   tactacacat  atcgcacgaa  tttccgtttg  ccgtttgtat  tttacgatat
        C  T  T  H  I  A  R    I  S  V    C  R  L  Y  F  T  I 2051   gttatttaat  gaatatgttt  catgtggttg  ttgcttaaaa  aaaaagtcga
        C  Y  L    M  N  M  F  H  V  V    V  A  -    K  K ⌊ S  R
              ⌈ NotI  ⌉⌈ EcoRI ➡
2101   cgcggccgcg  aa  (SEQ ID NO. 11)
        R  G  R ⌋  E  (SEQ ID NO. 12)
   EcoRI (NotI) Adapter
```

FIG. 10-3

```
          ┌ NcoI ┐
     7281 ccatggcact tacagaagaa aaacctattc gccccattgc caactttcct
          T  M  A   L  T  E  E   K  P  I   R  P  I  A  N  F  P
          Start codon 50 ccaagcattt ggggagatca gtttctcatc tatcaaaagc aagtagagca
          P  S  I   W  G  D  Q   F  L  I   Y  Q  K   Q  V  E 100 agggtggaa cagatagtga atgatttaaa aaaagaagtg cggcaactac
          Q  G  V  E   Q  I  V   N  D  L   K  K  E  V   R  Q  L 150 taaaagaagc tttggatatt cctatgaaac atgccaattt gttgaagctg
          L  K  E   A  L  D  I   P  M  K   H  A  N   L  L  K  L 200 attgatgaaa ttcaacgcct tggaataccg tatcactttg aacgggagat
          I  D  E   I  Q  R   L  G  I  P   Y  H  F   E  R  E 250 tgatcatgca ttgcaatgta tttatgaaac atatggtgat aactggaatg
          I  D  H  A   L  Q  C   I  Y  E   T  Y  G  D   N  W  N 300 gtgaccgctc ttccttatgg ttccgtctta tgcgaaagca aggatattat
          G  D  R   S  S  L  W   F  R  L   M  R  K   Q  G  Y  Y 350 gttacatgtg atgttttcaa taactataaa gacaaaaatg gagcgttcaa
          V  T  C   D  V  F   N  N  Y  K   D  K  N   G  A  F 400 gcaatcgtta gctaatgatg ttgaaggttt gcttgagttg tacgaagcaa
          K  Q  S  L   A  N  D   V  E  G   L  L  E  L   Y  E  A 450 cttctatgag ggtacctggg gagattatat tagaagatgc tcttggtttt
          T  S  M   R  V  P  G   E  I  I   L  E  D   A  L  G  F 500 acacgatctc gtcttagcat tatgacaaaa gatgcttttt ctacaaaccc
          T  R  S   R  L  S   I  M  T  K   D  A  F   S  T  N 550 cgctcttttt accgaaatac aacgggcact aaagcaaccc ctttggaaaa
          P  A  L  F   T  E  I   Q  R  A   L  K  Q  P   L  W  K 600 ggttgccaag aatagaggcg gcgcagtaca ttcctttcta tcaacaacaa
          R  L  P   R  I  E  A   A  Q  Y   I  P  F   Y  Q  Q  Q 650 gattctcata acaagacttt acttaaactt gctaagttag agttcaattt
          D  S  H   N  K  T   L  L  K  L   A  K  L   E  F  N 700 gcttcagtca ttgcacaagg aagagctcag ccatgtgtgc aaatggtgga
          L  L  Q  S   L  H  K   E  E  L   S  H  V  C   K  W  W 750 aagctttcga tatcaagaag aacgcacctt gtttaagaga tagaattgtt
          K  A  F   D  I  K  K   N  A  P   C  L  R   D  R  I  V 800 gaatgctact tttggggact aggttcaggc tatgagccac agtattcccg
          E  C  Y   F  W  G   L  G  S  G   Y  E  P   Q  Y  S 850 ggctagagtt ttcttcacaa aagctgttgc tgttataact cttatagatg
          R  A  R  V   F  F  T   K  A  V   A  V  I  T   L  I  D
```

FIG. 12-1

```
 900    acacttatga  tgcgtatggt  acttatgaag  aacttaagat  ctttactgaa
         D   T   Y   D   A   Y   G   T   Y   E   E   L   K   I   F   T   E 950    gctgttgaaa  ggtggtcaat  tacatgctta  gacacacttc  cagaatacat
         A   V   E   R   W   S   I   T   C   L   D   T   L   P   E   Y 1000    gaaaccgata  tacaaattat  tcatggatac  atacacagaa  atggaagaat
         M   K   P   I   Y   K   L   F   M   D   T   Y   T   E   M   E   E 1050    ttcttgcaaa  ggagggaaga  acagatctat  ttaactgcgg  caaagaattt
         F   L   A   K   E   G   R   T   D   L   F   N   C   G   K   E   F 1100    gtgaaagagt  ttgttagaaa  cctgatggtt  gaagcaaaat  gggcaaatga
         V   K   E   F   V   R   N   L   M   V   E   A   K   W   A   N 1150    gggacacata  ccaaccactg  aagagcatga  tccagttgta  atcattactg
         E   G   H   I   P   T   T   E   E   H   D   P   V   V   I   I   T 1200    gcggtgctaa  cctgcttaca  acaacttgtt  atcttggcat  gagtgatata
         G   G   A   N   L   L   T   T   T   C   Y   L   G   M   S   D   I 1250    ttcacaaaag  agtctgtcga  atgggctgtc  tctgcacctc  ctctttttag
         F   T   K   E   S   V   E   W   A   V   S   A   P   P   L   F 1300    atactcaggt  atacttggtc  gacgcctaaa  tgatctcatg  acccacaagg
         R   Y   S   G   I   L   G   R   R   L   N   D   L   M   T   H   K 1350    ccgagcaaga  aagaaaacat  agttcatcga  gccttgaaag  ttatatgaag
         A   E   Q   E   R   K   H   S   S   S   S   L   E   S   Y   M   K 1400    gaatataatg  tcaatgagga  gtatgcccaa  accttgattt  acaaggaagt
         E   Y   N   V   N   E   E   Y   A   Q   T   L   I   Y   K   E 1450    agaagatgtg  tggaaagata  taaaccgaga  gtacctcaca  actaaaaaca
         V   E   D   V   W   K   D   I   N   R   E   Y   L   T   T   K   N 1500    ttccaaggcc  gttattgatg  gctgtgatct  atttgtgcca  gtttcttgaa
         I   P   R   P   L   L   M   A   V   I   Y   L   C   Q   F   L   E 1550    gttcaatatg  caggaaagga  taacttcaca  cgtatgggag  acgaatacaa
         V   Q   Y   A   G   K   D   N   F   T   R   M   G   D   E   Y
                                                                    ┌ BamHI ┐
1600    acatctcata  aagtctctac  tcgtttatcc  tatgagtata  tgaggatcc
         K   H   L   I   K   S   L   L   V   Y   P   M   S   I   -   G   S
                                                                Stop codon
```
(SEQ ID NO. 13)
(SEQ ID NO. 14)

FIG. 12-2

SEQUENCE LISTING

<160> NUMBER OF SEQ ID NOS: 14

<210> SEQ ID NO 1
<211> LENGTH: 15
<212> TYPE: DNA
<213> ORGANISM: Artificial Sequence
<220> FEATURE:
<223> OTHER INFORMATION: EcoR I (Not I) adapter

<400> SEQUENCE: 1
gtcgacgcgg ccgcg                                                    15

<210> SEQ ID NO 2
<211> LENGTH: 19
<212> TYPE: DNA
<213> ORGANISM: Artificial Sequence
<220> FEATURE:
<223> OTHER INFORMATION: EcoR I (Not I) adapter

<400> SEQUENCE: 2
cagctgcgcc ggcgcttaa                                                19

<210> SEQ ID NO 3
<211> LENGTH: 27
<212> TYPE: DNA
<213> ORGANISM: Artificial Sequence
<220> FEATURE:
<223> OTHER INFORMATION: Sense primer (primer C) used in PCR
      amplification

<400> SEQUENCE: 3
gtcgacaaac catggcactt acagaag                                       27

<210> SEQ ID NO 4
<211> LENGTH: 32
<212> TYPE: DNA
<213> ORGANISM: Artificial Sequence
<220> FEATURE:
<223> OTHER INFORMATION: Antisense primer (primer D) used in PCR
      amplification

<400> SEQUENCE: 4
ggatggatcc tcatatactc ataggataaa cg                                 32

<210> SEQ ID NO 5
<211> LENGTH: 23
<212> TYPE: DNA
<213> ORGANISM: Artificial Sequence
<220> FEATURE:
<223> OTHER INFORMATION: Sense primer (primer G) used in PCR
      amplification

<400> SEQUENCE: 5
gaggatccat gtcacttaca gaa                                    23

<210> SEQ ID NO 6
<211> LENGTH: 24
<212> TYPE: DNA
<213> ORGANISM: Artificial Sequence
<220> FEATURE:
<223> OTHER INFORMATION: Antisense primer (primer H) used in PCR
      amplification

<400> SEQUENCE: 6
atggatcctc atatactcat agga                                   24

<210> SEQ ID NO 7
<211> LENGTH: 22
<212> TYPE: DNA
<213> ORGANISM: Artificial Sequence
<220> FEATURE:
<223> OTHER INFORMATION: Sense primer (primer E) used in PCR
      amplification

<400> SEQUENCE: 7
cgagaattca tgtcacttac ag                                     22

<210> SEQ ID NO 8
<211> LENGTH: 22
<212> TYPE: DNA
<213> ORGANISM: Artificial Sequence
<220> FEATURE:
<223> OTHER INFORMATION: Antisense primer (primer F) used in PCR
      amplification

<400> SEQUENCE: 8
ggatctcgag tcatatactc at                                     22

<210> SEQ ID NO 9
<211> LENGTH: 538
<212> TYPE: DNA
<213> ORGANISM: Artificial Sequence
<220> FEATURE:
<223> OTHER INFORMATION: Nucleotide sequence of probe generated by PCR
      with primers A and B

<400> SEQUENCE: 9
gatgagaatg ggaaatttaa ggaatcgtta gctaatgatg ttgaaggttt gcttgagttg     60
tacgaagcaa cttctatgag ggtacctggg gagattatat tagaagatgc tcttggtttt   120
acacgatctc gtcttagcat tatgacaaaa gatgcttttt ctacaaaccc cgctctttt    180 accgaaatac aacgggcact aaagcaaccc ctttggaaaa ggttgccaag aatagaggcg   240
gcgcagtaca ttcctttcta tcaacaacaa gattctcata caagacttt acttaaactt    300 gctaagttag agttcaattt gcttcagtca ttgcacaagg aagagctcag ccatgtgtgc   360
aaatggtgga agctttcga tatcaagaag aacgcacctt gtttaagaga tagaattgtt    420
gaatgctact tttggggact aggttcaggc tatgagccac agtattcccg ggctagagtt   480
ttcttcacaa aagctgttgc tgttataact cttatagacg acaccttcga cgctacgg    538

<210> SEQ ID NO 10
<211> LENGTH: 179
<212> TYPE: PRT
<213> ORGANISM: Artificial Sequence
<220> FEATURE:
<223> OTHER INFORMATION: Deduced amino acid sequence of probe generated by PCR with primers A and B

<400> SEQUENCE: 10

Asp Glu Asn Gly Lys Phe Lys Glu Ser Leu Ala Asn Asp Val Glu Gly
1               5                   10                  15

Leu Leu Glu Leu Tyr Glu Ala Thr Ser Met Arg Val Pro Gly Glu Ile
            20                  25                  30

Ile Leu Glu Asp Ala Leu Gly Phe Thr Arg Ser Arg Leu Ser Ile Met
        35                  40                  45

Thr Lys Asp Ala Phe Ser Thr Asn Pro Ala Leu Phe Thr Glu Ile Gln
    50                  55                  60

Arg Ala Leu Lys Gln Pro Leu Trp Lys Arg Leu Pro Arg Ile Glu Ala
65                  70                  75                  80

Ala Gln Tyr Ile Pro Phe Tyr Gln Gln Gln Asp Ser His Asn Lys Thr
                85                  90                  95

Leu Leu Lys Leu Ala Lys Leu Glu Phe Asn Leu Leu Gln Ser Leu His
            100                 105                 110

Lys Glu Glu Leu Ser His Val Cys Lys Trp Trp Lys Ala Phe Asp Ile
        115                 120                 125

Lys Lys Asn Ala Pro Cys Leu Arg Asp Arg Ile Val Glu Cys Tyr Phe
    130                 135                 140

Trp Gly Leu Gly Ser Gly Tyr Glu Pro Gln Tyr Ser Arg Ala Arg Val
145                 150                 155                 160

Phe Phe Thr Lys Ala Val Ala Val Ile Thr Leu Ile Asp Asp Thr Phe
                165                 170                 175

Asp Ala Thr

<210> SEQ ID NO 11
<211> LENGTH: 2112
<212> TYPE: DNA
<213> ORGANISM: Artemisia annua L.
<220> FEATURE:
<223> OTHER INFORMATION: Nucleotide sequence of a positive clone
      (amorphadiene synthase encoding gene) isolated from the cDNA
      library of induced A.annua

<400> SEQUENCE: 11
aattcgcggc cgcgtcgaca aatcatgtca cttacagaag aaaaacctat tcgccccatt      60 gccaacttc ctccaagcat ttggggagat cagtttctca tctatcaaaa gcaagtagag     120
caaggggtgg aacagatagt gaatgattta aaaaaagaag tgcggcaact actaaaagaa     180
gctttggata ttcctatgaa acatgccaat tgttgaagc tgattgatga aattcaacgc     240
cttggaatac cgtatcactt tgaacgggag attgatcatg cattgcaatg tatttatgaa     300
acatatggtg ataactggaa tggtgaccgc tcttccttat ggttccgtct tatgcgaaag     360
caaggatatt atgttacatg tgatgttttc aataactata agacaaaaa tggagcgttc     420 aagcaatcgt tagctaatga tgttgaaggt ttgcttgagt tgtacgaagc aacttctatg     480
agggtacctg gggagattat attagaagat gctcttggtt ttacacgatc tcgtcttagc     540
attatgacaa agatgctttt tctacaaac cccgctcttt ttaccgaaat acaacgggca     600
ctaaagcaac ccctttggaa aaggttgcca agaatagagg cggcgcagta cattcctttc     660
tatcaacaac aagattctca taacaagact ttacttaaac ttgctaagtt agagttcaat     720
ttgcttcagt cattgcacaa ggaagagctc agccatgtgt gcaaatggtg gaaagctttc     780
gatatcaaga agaacgcacc ttgtttaaga gatagaattg ttgaatgcta cttttgggga     840

```
ctaggttcag gctatgagcc acagtattcc cgggctagag ttttcttcac aaaagctgtt    900
gctgttataa ctcttataga tgacacttat gatgcgtatg gtacttatga agaacttaag    960
atctttactg aagctgttga aaggtggtca attacatgct agacacact tccagaatac    1020
atgaaaccga tatacaaatt attcatggat acatacacag aaatggaaga atttcttgca    1080
aaggagggaa gaacagatct atttaactgc ggcaaagaat tgtgaaaga gtttgttaga    1140
aacctgatgg ttgaagcaaa atgggcaaat gagggacaca taccaaccac tgaagagcat    1200
gatccagttg taatcattac tggcggtgct aacctgctta caacaacttg ttatcttggc    1260
atgagtgata tattcacaaa agagtctgtc gaatgggctg tctctgcacc tcctcttttt    1320
agatactcag gtatacttgg tcgacgccta aatgatctca tgacccacaa ggccgagcaa    1380
gaaagaaaac atagttcatc gagccttgaa agttatatga aggaatataa tgtcaatgag    1440
gagtatgccc aaaccttgat ttacaaggaa gtagaagatg tgtggaaaga tataaaccga    1500
gagtacctca caactaaaaa cattccaagg ccgttattga tggctgtgat ctatttgtgc    1560
cagtttcttg aagttcaata tgcaggaaag gataacttca cacgtatggg agacgaatac    1620
aaacatctca taaagtctct actcgtttat cctatgagta tatgactacc aatccttcgt    1680
gcatagccta tcaattatat tgaaagggtt aactatgcac gtctctatgg agagaatttc    1740
tcaagctatt tggtgtttct tgctggcaat aataaatcag acgcataaaa ttgtattgaa    1800
ctatatgccg atagctattt aaagttatta tacaactaaa atattcaaca atggtattat    1860
acttttactt tgtacaaaag caaaagtaca ctactgttat gtaacatttt agttctatga    1920
tactttagtt acgaatcggc ttatatacat tgatacactt ttatgcagaa aaccctagta    1980
aataaaaagt cgatatcttg tactacacat atcgcacgaa tttccgtttg ccgtttgtat    2040
tttacgatat gttatttaat gaatatgttt catgtggttg ttgcttaaaa aaaaagtcga    2100
cgcggccgcg aa                                                       2112
```

<210> SEQ ID NO 12
<211> LENGTH: 697
<212> TYPE: PRT
<213> ORGANISM: Artemisia annua L.
<220> FEATURE:
<223> OTHER INFORMATION: Deduced amino acid sequence of a positive clone (amorphadiene synthase encoding gene) isolated from the cDNA library of induced A.annua

<400> SEQUENCE: 12

```
Asn Ser Arg Pro Arg Arg Gln Ile Met Ser Leu Thr Glu Glu Lys Pro
  1               5                  10                  15

Ile Arg Pro Ile Ala Asn Phe Pro Pro Ser Ile Trp Gly Asp Gln Phe
                 20                  25                  30

Leu Ile Tyr Gln Lys Gln Val Glu Gln Gly Val Glu Gln Ile Val Asn
         35                  40                  45

Asp Leu Lys Lys Glu Val Arg Gln Leu Leu Lys Glu Ala Leu Asp Ile
     50                  55                  60

Pro Met Lys His Ala Asn Leu Leu Lys Leu Ile Asp Glu Ile Gln Arg
 65                  70                  75                  80

Leu Gly Ile Pro Tyr His Phe Glu Arg Glu Ile Asp His Ala Leu Gln
                 85                  90                  95

Cys Ile Tyr Glu Thr Tyr Gly Asp Asn Trp Asn Gly Asp Arg Ser Ser
                100                 105                 110

Leu Trp Phe Arg Leu Met Arg Lys Gln Gly Tyr Tyr Val Thr Cys Asp
            115                 120                 125
```

-continued

```
Val Phe Asn Asn Tyr Lys Asp Lys Asn Gly Ala Phe Lys Gln Ser Leu
    130                 135                 140
Ala Asn Asp Val Glu Gly Leu Leu Glu Leu Tyr Glu Ala Thr Ser Met
145                 150                 155                 160
Arg Val Pro Gly Glu Ile Ile Leu Glu Asp Ala Leu Gly Phe Thr Arg
                165                 170                 175
Ser Arg Leu Ser Ile Met Thr Lys Asp Ala Phe Ser Thr Asn Pro Ala
            180                 185                 190
Leu Phe Thr Glu Ile Gln Arg Ala Leu Lys Gln Pro Leu Trp Lys Arg
        195                 200                 205
Leu Pro Arg Ile Glu Ala Ala Gln Tyr Ile Pro Phe Tyr Gln Gln Gln
    210                 215                 220
Asp Ser His Asn Lys Thr Leu Leu Lys Leu Ala Lys Leu Glu Phe Asn
225                 230                 235                 240
Leu Leu Gln Ser Leu His Lys Glu Glu Leu Ser His Val Cys Lys Trp
                245                 250                 255
Trp Lys Ala Phe Asp Ile Lys Lys Asn Ala Pro Cys Leu Arg Asp Arg
            260                 265                 270
Ile Val Glu Cys Tyr Phe Trp Gly Leu Gly Ser Gly Tyr Glu Pro Gln
        275                 280                 285
Tyr Ser Arg Ala Arg Val Phe Phe Thr Lys Ala Val Ala Val Ile Thr
    290                 295                 300
Leu Ile Asp Asp Thr Tyr Asp Ala Tyr Gly Thr Tyr Glu Glu Leu Lys
305                 310                 315                 320
Ile Phe Thr Glu Ala Val Glu Arg Trp Ser Ile Thr Cys Leu Asp Thr
                325                 330                 335
Leu Pro Glu Tyr Met Lys Pro Ile Tyr Lys Leu Phe Met Asp Thr Tyr
            340                 345                 350
Thr Glu Met Glu Glu Phe Leu Ala Lys Glu Gly Arg Thr Asp Leu Phe
        355                 360                 365
Asn Cys Gly Lys Glu Phe Val Lys Glu Phe Val Arg Asn Leu Met Val
    370                 375                 380
Glu Ala Lys Trp Ala Asn Glu Gly His Ile Pro Thr Thr Glu Glu His
385                 390                 395                 400
Asp Pro Val Val Ile Ile Thr Gly Gly Ala Asn Leu Leu Thr Thr Thr
                405                 410                 415
Cys Tyr Leu Gly Met Ser Asp Ile Phe Thr Lys Glu Ser Val Glu Trp
            420                 425                 430
Ala Val Ser Ala Pro Pro Leu Phe Arg Tyr Ser Gly Ile Leu Gly Arg
        435                 440                 445
Arg Leu Asn Asp Leu Met Thr His Lys Ala Glu Gln Glu Arg Lys His
    450                 455                 460
Ser Ser Ser Ser Leu Glu Ser Tyr Met Lys Glu Tyr Asn Val Asn Glu
465                 470                 475                 480
Glu Tyr Ala Gln Thr Leu Ile Tyr Lys Glu Val Glu Asp Val Trp Lys
                485                 490                 495
Asp Ile Asn Arg Glu Tyr Leu Thr Thr Lys Asn Ile Pro Arg Pro Leu
            500                 505                 510
Leu Met Ala Val Ile Tyr Leu Cys Gln Phe Leu Glu Val Gln Tyr Ala
        515                 520                 525
Gly Lys Asp Asn Phe Thr Arg Met Gly Asp Glu Tyr Lys His Leu Ile
    530                 535                 540
```

-continued

```
Lys Ser Leu Leu Val Tyr Pro Met Ser Ile Leu Pro Ile Leu Arg Ala
545                 550                 555                 560

Pro Ile Asn Tyr Ile Glu Arg Val Asn Tyr Ala Arg Leu Tyr Gly Glu
                565                 570                 575

Asn Phe Ser Ser Tyr Leu Val Phe Leu Ala Gly Asn Asn Lys Ser Asp
            580                 585                 590

Ala Asn Cys Ile Glu Leu Tyr Ala Asp Ser Tyr Leu Lys Leu Leu Tyr
        595                 600                 605

Asn Asn Ile Gln Gln Trp Tyr Tyr Thr Phe Thr Leu Tyr Lys Ser Lys
    610                 615                 620

Ser Thr Leu Leu Leu Cys Asn Ile Leu Val Leu Tyr Phe Ser Tyr Glu
625                 630                 635                 640

Ser Ala Tyr Ile His Tyr Thr Phe Met Gln Lys Thr Leu Val Asn Lys
                645                 650                 655

Lys Ser Ile Ser Cys Thr Thr His Ile Ala Arg Ile Ser Val Cys Arg
            660                 665                 670

Leu Tyr Phe Thr Ile Cys Tyr Leu Met Asn Met Phe His Val Val Val
        675                 680                 685

Ala Lys Lys Ser Arg Arg Gly Arg Glu
    690                 695

<210> SEQ ID NO 13
<211> LENGTH: 1649
<212> TYPE: DNA
<213> ORGANISM: Artificial Sequence
<220> FEATURE:
<223> OTHER INFORMATION: Nucleotide sequence of the amorphadiene
      synthase encoding gene, between start and stop codon, obtained by
      PCR with primers C and D

<400> SEQUENCE: 13
ccatggcact tacagaagaa aaacctattc gccccattgc caactttcct ccaagcattt      60
ggggagatca gtttctcatc tatcaaaagc aagtagagca aggggtggaa cagatagtga    120
atgatttaaa aaaagaagtg cggcaactac taaaagaagc tttggatatt cctatgaaac    180
atgccaattt gttgaagctg attgatgaaa ttcaacgcct tggaataccg tatcactttg    240
aacgggagat tgatcatgca ttgcaatgta tttatgaaac atatggtgat aactggaatg    300
gtgaccgctc ttccttatgg ttccgtctta tgcgaaagca aggatattat gttacatgtg    360
atgttttcaa taactataaa gacaaaaatg gagcgttcaa gcaatcgtta gctaatgatg    420
ttgaaggttt gcttgagttg tacgaagcaa cttctatgag ggtacctggg gagattatat    480
tagaagatgc tcttggtttt acacgatctc gtcttagcat tatgacaaaa gatgcttttt    540
ctacaaaccc cgctcttttt accgaaatac aacgggcact aaagcaaccc ctttggaaaa    600
ggttgccaag aatagaggcg gcgcagtaca ttcctttcta tcaacaacaa gattctcata    660
acaagacttt acttaaactt gctaagttag agttcaattt gcttcagtca ttgcacaagg    720
aagagctcag ccatgtgtgc aaatggtgga agctttcga tatcaagaag aacgcacctt    780
gtttaagaga tagaattgtt gaatgctact tttgggact aggttcaggc tatgagccac    840
agtattcccg ggctagagtt ttcttcacaa aagctgttgc tgttataact cttatagatg    900
acacttatga tgcgtatggt acttatgaag aacttaagat ctttactgaa gctgttgaaa    960
ggtggtcaat tacatgctta gacacacttc cagaatacat gaaaccgata tacaaattat   1020
tcatggatac atacacagaa atggaagaat tccttgcaaa ggagggaaga acagatctat   1080
ttaactgcgg caaagaattt gtgaaagagt ttgttagaaa cctgatggtt gaagcaaaat   1140
```

-continued

```
gggcaaatga gggacacata ccaaccactg aagagcatga tccagttgta atcattactg    1200
gcggtgctaa cctgcttaca acaacttgtt atcttggcat gagtgatata ttcacaaaag    1260
agtctgtcga atgggctgtc tctgcacctc ctcttttag atactcaggt atacttggtc     1320
gacgcctaaa tgatctcatg acccacaagg ccgagcaaga aagaaaacat agttcatcga    1380
gccttgaaag ttatatgaag gaatataatg tcaatgagga gtatgcccaa accttgattt    1440
acaaggaagt agaagatgtg tggaaagata taaaccgaga gtacctcaca actaaaaaca    1500
ttccaaggcc gttattgatg gctgtgatct atttgtgcca gtttcttgaa gttcaatatg    1560
caggaaagga taacttcaca cgtatgggag acgaatacaa acatctcata aagtctctac    1620
tcgtttatcc tatgagtata tgaggatcc                                      1649
```

<210> SEQ ID NO 14
<211> LENGTH: 549
<212> TYPE: PRT
<213> ORGANISM: Artificial Sequence
<220> FEATURE:
<223> OTHER INFORMATION: Deduced amino acid sequence of the amorphadiene
      synthase encoding gene, between start and stop codon, obtained by
      PCR with primers C and D

<400> SEQUENCE: 14

```
Thr Met Ala Leu Thr Glu Glu Lys Pro Ile Arg Pro Ile Ala Asn Phe
              5                   10                  15

Pro Pro Ser Ile Trp Gly Asp Gln Phe Leu Ile Tyr Gln Lys Gln Val
         20                  25                  30

Glu Gln Gly Val Glu Gln Ile Val Asn Asp Leu Lys Lys Glu Val Arg
     35                  40                  45

Gln Leu Leu Lys Glu Ala Leu Asp Ile Pro Met Lys His Ala Asn Leu
 50                  55                  60

Leu Lys Leu Ile Asp Glu Ile Gln Arg Leu Gly Ile Pro Tyr His Phe
 65                  70                  75                  80

Glu Arg Glu Ile Asp His Ala Leu Gln Cys Ile Tyr Glu Thr Tyr Gly
             85                  90                  95

Asp Asn Trp Asn Gly Asp Arg Ser Ser Leu Trp Phe Arg Leu Met Arg
        100                 105                 110

Lys Gln Gly Tyr Tyr Val Thr Cys Asp Val Phe Asn Asn Tyr Lys Asp
    115                 120                 125

Lys Asn Gly Ala Phe Lys Gln Ser Leu Ala Asn Asp Val Glu Gly Leu
130                 135                 140

Leu Glu Leu Tyr Glu Ala Thr Ser Met Arg Val Pro Gly Glu Ile Ile
145                 150                 155                 160

Leu Glu Asp Ala Leu Gly Phe Thr Arg Ser Arg Leu Ser Ile Met Thr
                165                 170                 175

Lys Asp Ala Phe Ser Thr Asn Pro Ala Leu Phe Thr Glu Ile Gln Arg
            180                 185                 190

Ala Leu Lys Gln Pro Leu Trp Lys Arg Leu Pro Arg Ile Glu Ala Ala
        195                 200                 205

Gln Tyr Ile Pro Phe Tyr Gln Gln Asp Ser His Asn Lys Thr Leu
    210                 215                 220

Leu Lys Leu Ala Lys Leu Glu Phe Asn Leu Leu Gln Ser Leu His Lys
225                 230                 235                 240

Glu Glu Leu Ser His Val Cys Lys Trp Trp Lys Ala Phe Asp Ile Lys
                245                 250                 255
```

```
Lys Asn Ala Pro Cys Leu Arg Asp Arg Ile Val Glu Cys Tyr Phe Trp
            260                 265                 270
Gly Leu Gly Ser Gly Tyr Glu Pro Gln Tyr Ser Arg Ala Arg Val Phe
            275                 280                 285
Phe Thr Lys Ala Val Ala Val Ile Thr Leu Ile Asp Asp Thr Tyr Asp
            290                 295                 300
Ala Tyr Gly Thr Tyr Glu Glu Leu Lys Ile Phe Thr Glu Ala Val Glu
305                 310                 315                 320
Arg Trp Ser Ile Thr Cys Leu Asp Thr Leu Pro Glu Tyr Met Lys Pro
                325                 330                 335
Ile Tyr Lys Leu Phe Met Asp Thr Tyr Thr Glu Met Glu Glu Phe Leu
                340                 345                 350
Ala Lys Glu Gly Arg Thr Asp Leu Phe Asn Cys Gly Lys Glu Phe Val
                355                 360                 365
Lys Glu Phe Val Arg Asn Leu Met Val Glu Ala Lys Trp Ala Asn Glu
            370                 375                 380
Gly His Ile Pro Thr Thr Glu Glu His Asp Pro Val Val Ile Ile Thr
385                 390                 395                 400
Gly Gly Ala Asn Leu Leu Thr Thr Thr Cys Tyr Leu Gly Met Ser Asp
                405                 410                 415
Ile Phe Thr Lys Glu Ser Val Glu Trp Ala Val Ser Ala Pro Pro Leu
            420                 425                 430
Phe Arg Tyr Ser Gly Ile Leu Gly Arg Arg Leu Asn Asp Leu Met Thr
            435                 440                 445
His Lys Ala Glu Gln Glu Arg Lys His Ser Ser Ser Ser Leu Glu Ser
    450                 455                 460
Tyr Met Lys Glu Tyr Asn Val Asn Glu Glu Tyr Ala Gln Thr Leu Ile
465                 470                 475                 480
Tyr Lys Glu Val Glu Asp Val Trp Lys Asp Ile Asn Arg Glu Tyr Leu
                485                 490                 495
Thr Thr Lys Asn Ile Pro Arg Pro Leu Leu Met Ala Val Ile Tyr Leu
                500                 505                 510
Cys Gln Phe Leu Glu Val Gln Tyr Ala Gly Lys Asp Asn Phe Thr Arg
            515                 520                 525
Met Gly Asp Glu Tyr Lys His Leu Ile Lys Ser Leu Leu Val Tyr Pro
            530                 535                 540
Met Ser Ile Gly Ser
545
```

US 7,541,172 B2

TRANSGENIC AMORPHA-4, 11-DIENE SYNTHESIS

This application is a divisional of U.S. application Ser. No. 09/763,822, filed Apr. 24, 2001, now U.S. Pat. No. 7,091,027, which is a 35 U.S.C. § 371 filing of PCT Application PCT/EP99/06302, filed Aug. 27, 1999, which claims priority to European Application No. 98202854.0, filed Aug. 27, 1998. All of these applications are incorporated herein by reference in their entirety for any purpose.

BACKGROUND OF THE INVENTION

1. Field of the Invention

The present invention relates to a DNA sequence, a polypeptide encoded by this sequence, and to the use of said DNA sequence and polypeptide in the production of amorphadiene.

2. Description of the Related Art

Human malaria is a commonly occurring widespread infectious disease, caused in 85% of the cases by *Plasmodium falciparum*. This parasite is responsible for the most lethal form of malaria, malaria tropicana. Each year, malaria causes clinical illness, often very severe, in over 100 million people of which eventually over 1 million individuals will die. Approximately 40% of the world's population is at risk of malaria infection (as estimated by the World Health Organization).

Malaria has traditionally been treated with quinolines, such as quinine, chloroquine, mefloquine and primaquine, and with antifolates. Unfortunately, most *P. falciparum* strains have become resistant to chloroquine, and some have developed resistance to mefloquine and halofantrine as well. Thus, novel antimalarial drugs to which resistant parasites are sensitive are urgently needed. Artemisinin, as well as its semi-synthetic derivatives are promising candidates here.

Artemisinin (FIG. 1), [3R-(3α,5aβ,6β,8aβ, 9α,12β, 12aR*)]-Octahydro-3,6,9-trimethyl-3,12-epoxy-12H-pyrano[4,3-j]-1,2-benzodioxepin-10(3H)-one; molecular weight 282.35), also called arteannuin, qinghaosu or QHS, is a sesquiterpene lactone endoperoxide isolated from the aerial parts of the plant *Artemisia annua* L.

*Artemisia annua* L., also known as quinghao (Chinese), annual or sweet wormwood, or sweet annie is an annual herb native to Asia. *A. annua*, a member of the Asteraceae, belongs to the tribe Anthemideae of the Asteroideae, and is a large herb often reaching more than 2.0 m in height. It is usually single-stemmed with alternating branches. The aromatic leaves are deeply dissected and range from 2.5 to 5 cm in length. Artemisinin is mainly produced in the leaves as a secondary metabolite at a concentration of 0.01-0.6% on a dry weight base in natural populations. Artemisinin is unique to the plant *A. annua* with one possible exception of *A. apiacea* L. The *A. annua* used in this invention is of Vietnamese origin.

Because of its low concentration in plants, artemisinin is a relatively expensive resource for a drug. Current research has thus been aimed at producing artemisinin at a larger scale by organic synthesis. However, because artemisinin consist of seven chiral carbon atoms, theoretically $2^7=128$ isomers can be formed of which only one is identical to artemisinin. Because of this complex structure of artemisinin, production of this compound by organic synthesis is not profitable from a commercial point of view.

Genetic engineering of the biosynthetic pathway of artemisinin may give rise to higher artemisinin levels in plants. To be able to interfere in the biosynthesis of artemisinin, the biosynthetic pathway has to be known, either completely or partially. Several attempts to elucidate the entire biosynthetic pathway have been undertaken. Until now, however, the exact pathway has remained largely unknown.

In the research that led to the present invention, a unique pathway has been discovered which has not been published before. This pathway involves inter alia the formation of the artemisinin precursors amorpha-4,11-diene (1β,6β,7β, 10αH-amorpha-4,11-diene) and the hydroperoxide of dihydroarteannuic acid. These precursors that were found in *A. annua* have not been described before in literature.

Figure 2:
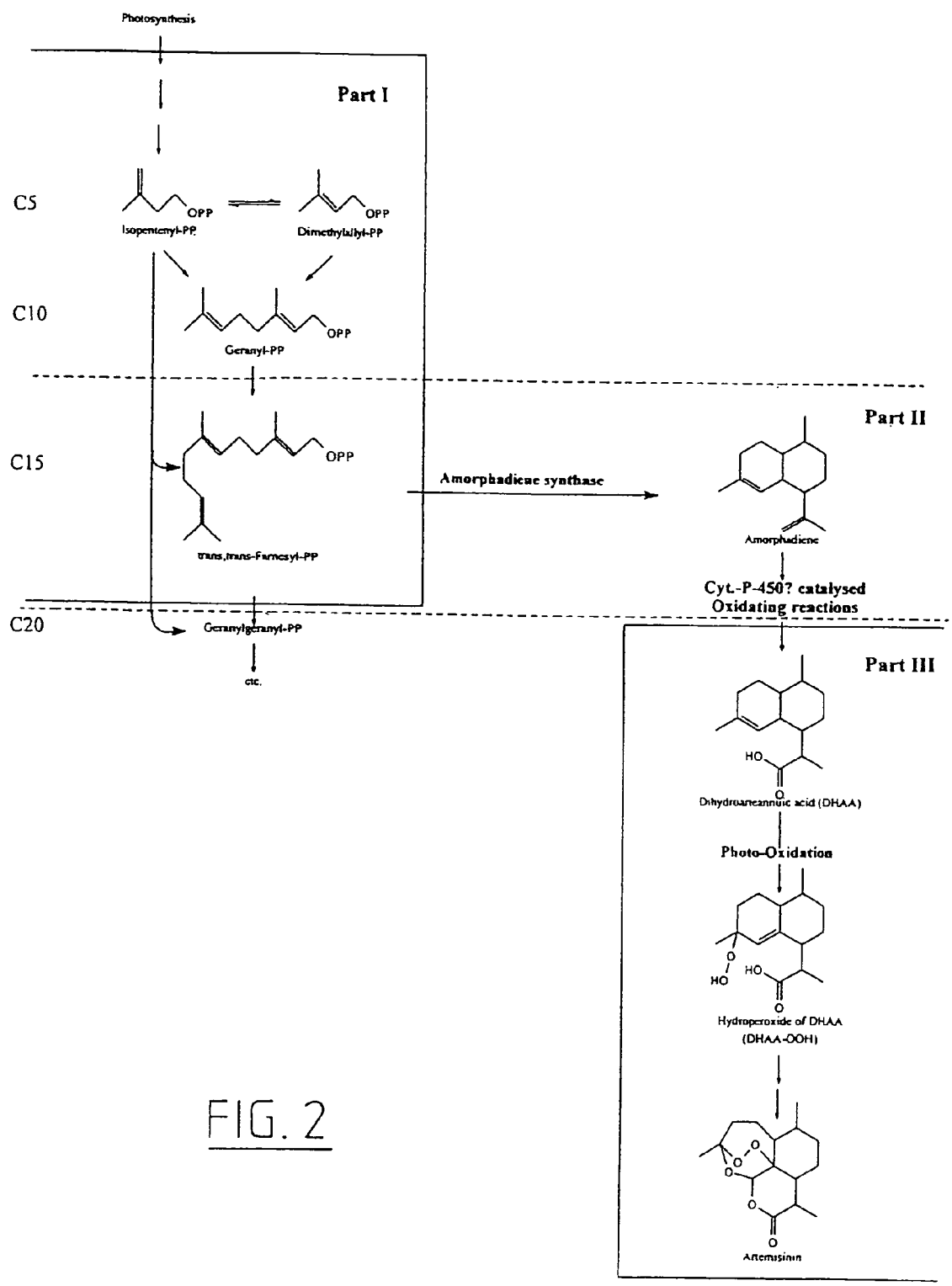

From literature it is known that terpene cyclases (synthases) are branch point enzymes, which likely play an important role in terpenoid biosynthesis. The working hypothesis for this invention is thus that over-expression of such a branch point enzyme (terpene cyclase) may increase terpenoid production in an organism. Factors that may influence the success of such an approach are, in the case of artemisinin, the number and nature of the subsequent biosynthetic steps leading to artemisinin. FIG. 2 shows the biosynthetic pathway of artemisinin as postulated by the present inventors. This pathway is divided into three parts:

The first part (Part I) represents the terpenoid (Isoprenoid) pathway. This pathway is a general pathway. Farnesyl diphosphate (farnesyl pyrophosphate) (FPP), for example, is present in every living organism and it is the precursor of a large number of primary and secondary metabolites. It has been established that FPP is the precursor of all sesquiterpenes. Thus, by definition FPP is the precursor of artemisinin.

Part II displays the cyclization of the general precursor FPP into the highly specific precursor amorpha-4,11-diene (also referred to as amorphadiene), the first specific precursor of artemisinin. In this pathway amorphadiene synthase is a branch point enzyme, having a key position in the biosynthetic pathway of artemisinin.

In part III, dihydroarteannuic acid (DHAA), also called dihydroartemisinic acid, is photo-oxidatively converted into its hydroperoxide (DHAA-OOH). This hydroperoxide of DHAA will spontaneously oxidize into artemisinin. No enzymes are involved in this part of the pathway and therefore it is impossible to alter artemisinin production by over-expression of genes involved in this part of the pathway.

Figure 3:
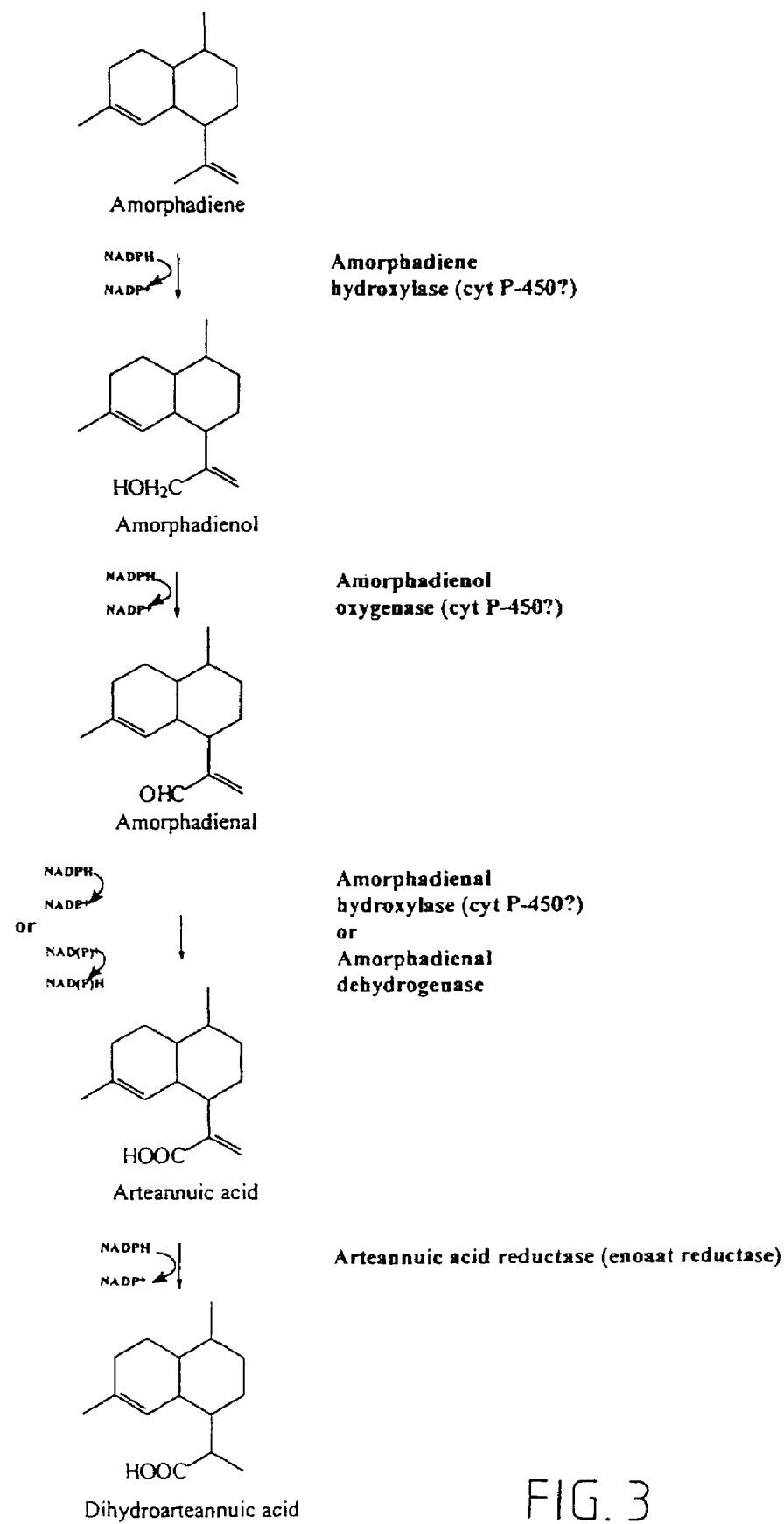

Cytochrome P-450 catalyzed enzymes and an enoate reductase are probably involved in the conversion of amorphadiene into DHAA, the transition state between part II and part III (see FIG. 3). Because no intermediates of this part of the pathway are known or present (accumulated) in detectable amounts, in the plant, (except arteannuic acid, also called artemisinic acid or 4,11(13)-amorphadien-12-oic acid) it is likely that these precursors are very rapidly converted into DHAA. A rate limiting step in this part of the pathway is not very likely.

Taking all these aspects into account the inventors concluded that the most logical step to be altered by genetic interfering, is the conversion (cyclization) of FPP into amorphadiene by amorphadiene synthase.

The object of the present invention is therefore to provide a way in which artemisinin can be obtained via an at least partially biological route.

This object is achieved by the provision of a DNA sequence which exhibits at least a 70% homology to the sequence as shown in FIG. 12, and which codes for a polypeptide having the biological activity of the enzyme amorphadiene synthase.

The biological activity of the enzyme amorphadiene synthase relates to the conversion of the general precursor farnesyl pyrophosphate (FPP) into the specific artemisinin precursor amorpha-4,11-diene, which, in *A. annua*, is further converted to artemisinin. Suitable genes according to the invention can be selected by testing the expression product of the gene for its ability to convert FPP into amorpha-4,11-diene.

By transforming a suitable host cell with the DNA sequence of the invention, the conversion of farnesyl pyrophosphate (FPP) into the highly specific precursor amorphadiene can be increased or induced if this conversion route is not naturally present in the organism. In the latter case, the organism should comprise or be able to produce FPP. Suitable host cells are for example bacterial cells, such as *E.coli*, yeast cells like *Saccharomyces cerevisiae* or *Pichia pastoris* and in particular oleaginous yeasts, like *Yarrowia lipolytica*, or plant cells such as those of *A.annua*.

Several plants are capable of producing large amounts of FPP making them potential organisms for amorphadiene production.

The potential oleaginous yeast host cells, like, for example, *Yarrowia lipolytica* and *Cryptococcus curvatus*, have the capacity to accumulate up to about 50%. (dry weight) of storage carbohydrates in oil bodies, making them very interesting candidates as production organisms for large quantities of terpenes. According to the invention, a way to obtain high levels of terpene accumulation is for example by means of re-direction of the metabolic flux in favor of the formation of amorpha-4,11-diene.

In analogy to the approach of an increased carotenoid production by the food yeast *Candida utilis* through metabolic engineering of the isoprenoid pathway as done by Shimada et al. (Appl. Environ. Microbiol. 64, 2676-2680 (1998)) the target genes according to the invention are acetyl CoA carboxylase (ACC, disruption), hydroxy-methyl-glutaryl CoA reductase (HMGR, over-expression), and squalene synthase (SQS, disruption) to obtain an increase of the precursor supplies, and amorpha-4,11-diene synthase over-expression to obtain accumulation of amorphadiene in such yeast cells. Because several expression systems (for example Muller et al., Yeast 14, 1267-1283 (1998); Park et al., The Journal of Biological Chemistry 272, 6876-6881 (1997); Tharaud et al., Gene 121, 111-119 (1992)) and transformation systems (for example Chen et al., Appl. Microbiol. Biotechnol. 48, 232-235 (1997)) are known for *Y.lipolytica* in literature, transformation and expression of the previously mentioned target genes in *Y.lipolytica* is possible without serious technical problems.

By adding FPP to a culture medium further comprising the enzyme of the invention (isolated as described in example 1), or transformed cells, e.g. *E.coli*, comprising the DNA sequence of the invention (as described in examples 3 and 4), which is expressed, FPP is converted into amorphadiene. Amorphadiene can then be used as a starting material for the production of artemisinin.

Transformed cells in which amorphadiene is produced as a result of the expression of amorphadiene synthase of the invention can be used either in disrupted form, by for example sonication, or as intact cells, as a source of amorphadiene.

Over-expression of the amorphadiene synthase encoding gene in *A.annua* will increase artemisinin production, because the terpene cyclase is expected to be the rate limiting step.

The results of the present research (postulated biosynthetic pathway of artemisinin) make the presence of a single major rate limiting step at the place of the amorphadiene synthase clear. Over-expression of the amorphadiene synthase encoding gene can increase the production of artemisinin in *A.annua*.

Figure 4:
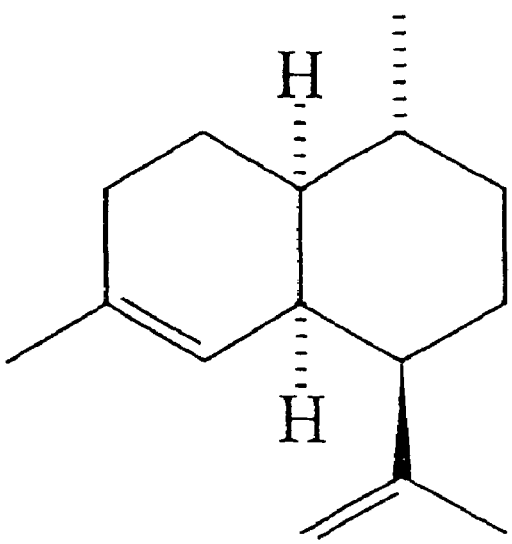

The chemical structure of the first specific precursor of artemisinin, a cyclization product of FPP, was not known in literature. Neither has anyone so far detected such a compound in *A.annua*. Nevertheless it was possible to predict a likely structure for this cyclization product, based on the structure of DHAA and arteannuic acid (FIG. 3). The structure predicted in this way was consistent with a compound which is known in literature as 4,11-amorphadiene (J. D. Connelly & R. A. Hill in: Dictionary of terpenoids, Chapmann and Hill, London, England), as depicted in FIG. 4. This compound, isolated from *Viguiera oblonqifolia*, has previously been described by Bohlmann et al. under the incorrect name cadina-4,11-diene (Phytochemistry 23(5) 1183-1184 (1984)). Starting from arteannuic acid (isolated from *A.annua*), it was possible to synthesize amorphadiene. Amorphadiene obtained in this way was in all chemical and physical aspects identical to amorphadiene as described by Bohlmann et al., and this standard was used to show the presence of amorphadiene in a terpene extract of *A.annua*.

A further object of the present invention is to provide a polypeptide having the biological activity of the enzyme amorphadiene synthase, obtainable by a process as described in example 1. This polypeptide can be used to convert FPP into amorphadiene which subsequently can be converted into artemisinin. Conversion can take place either in planta, when the polypeptide amorphadiene synthase is expressed in a plant that contains the necessary enzymes to further convert amorphadiene into artemisinin, or in vitro when FPP and the polypeptide (either in isolated form or as an expression product in a cell) are brought together in an incubation mixture.

Amorphadiene, produced by a suitable host organism transformed with the DNA sequence of the invention as precursor, can subsequently be chemically converted to dihydroarteannuic acid. Dihydroarteannuic acid per se can be used or in the production of artemisinin.

The chemical conversion of amorphadiene into dihydroarteannuic acid (FIG. 15) starts with the enantio-, stereo- and regioselective (anti-markownikoff) hydroboration of amorphadiene with $BH_3$, yielding a trialkylborane, followed by an oxidation of the trialkylborane with $NaOH/H_2O_2$ yielding the alcohol (Advanced Organic Chemistry, Jerry March, 4th Edition, Wiley, 1992). A mild oxidation of the alcohol to the acid can be obtained by PDC (pyridinium dichromate) without attacking the second double bond (FIG. 15) (Organic Synthesis, M. B. Smith, 1st Edition, McGraw-Hill, 1994).

Many genes encoding enzymes involved in the biosynthetic pathway of farnesyl diphosphate are cloned and known in literature. For *A.annua*, for example, the sequence of the farnesyl diphosphate synthase encoding gene is known in literature (Y. Matsushita, W-K. Kang and V. Charlwood Gene, 172 (1996) 207-209). A further approach to introduce or increase the amorphadiene production in an organism, is to transform such an organism (for example *A.annua*) simultaneously with the DNA sequence of the invention with one or more genes involved in the biosynthesis of farnesyl diphosphate. The expression of a fusion protein of amorphadiene synthase and farnesyl diphosphate synthase may be an example here.

(Sesqui)terpenes, such as amorphadiene, are also known as flavor and fragrance compounds in the food and perfume industry. In addition, terpenes play a role in plant-insect interactions, such as the attraction or repulsion of insects by plants. Furthermore, dihydro-arteannuic acid, which is an intermediate in the metabolic route from amorphadiene into artemisinin in *A.annua*, can be used as an antioxidant.

Amorphadiene, obtained by (over)expression of the DNA sequence of the invention, or by using the polypeptide (amorphadiene synthase) of the invention, can be applied for these purposes as well.

The plants that can be used for this invention are preferably plants already producing artemisinin. A prime example is *Artemisia annua*, as this species contains the remainder of the pathway leading to artemisinin. However, this invention may also be used for the production of amorphadiene in plants, which, as mentioned before, can be used as a flavor or fragrance compound or biocide, or can be converted to artemisinin, either chemically or by bioconversion using microorganisms, yeasts or plant cells.

The plant that can be used for the production of amorphadiene is preferably a plant already producing sesquiterpenes, as these plants already have the basic pathway and storage compartments available, or a plant in which the biosynthesis of sesquiterpenoids can be induced by elicitation. The methods of this invention are readily applicable via conventional techniques to numerous plant species, including for example species from the genera *Carum, Cichorium, Daucus, Juniperus, Chamomilla, Lactuca, Pogostemon* and *Vetiveria*, and species of the inducible (by elicitation) sesquiterpenoid phytoalexin producing genera *Capsicum, Gossyium, Lycopersicon, Nicotiana, Phleum, Solanum* and *Ulmus*. However, also common agricultural crops like soybean, sunflower and rapeseed are interesting candidates here.

The invention will be further illustrated by the following examples, but will not be limited thereto. In the examples reference is made to the following figures:

FIG. 1: Structural formula of artemisinin.

FIG. 2: Postulated biosynthetic pathway of artemisinin in *A.annua*.

FIG. 3: Transition between part II and III of FIG. 2: hypothetical conversion of amorphadiene into dihydroarteannuic acid in *A.annua*.

FIG. 4: Structural formula of amorpha-4,11-diene.

Figure 5:
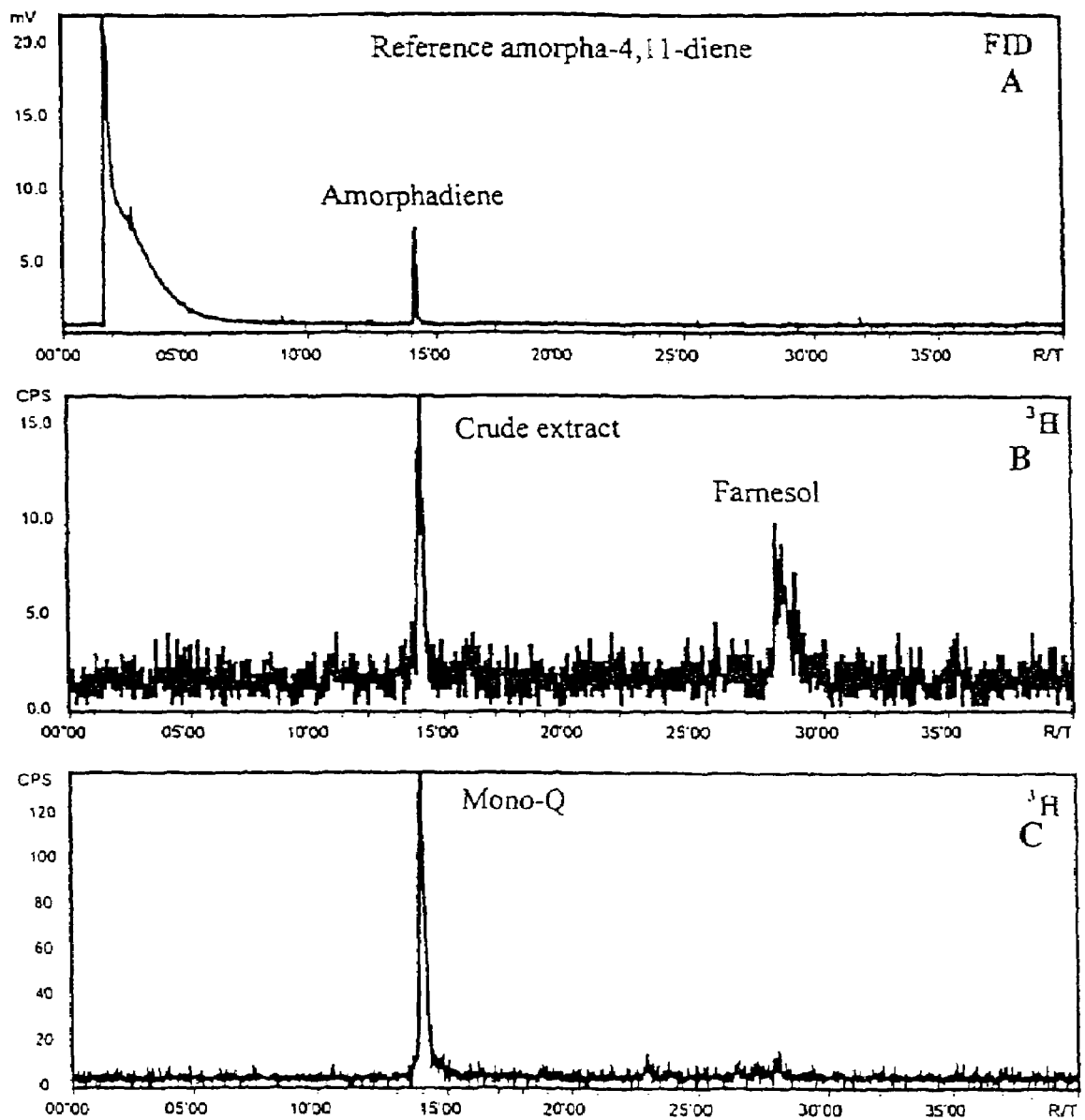

FIG. 5: Radio-GC chromatograms of the [$^3$H]-FPP-assays. A. Flame Ionization Detector (FID) signal of amorphadiene (reference). B. Radio signals of the $^3$H labeled assay products amorphadiene (retention time 14 min.) and farnesol (as a product of aspecific phosphohydrolase activity, retention time 28 min.) obtained with crude enzyme extract. C. Radio signal of the $^3$H labeled assay product amorphadiene obtained with Mono-Q purified enzyme extract.

Figure 6:
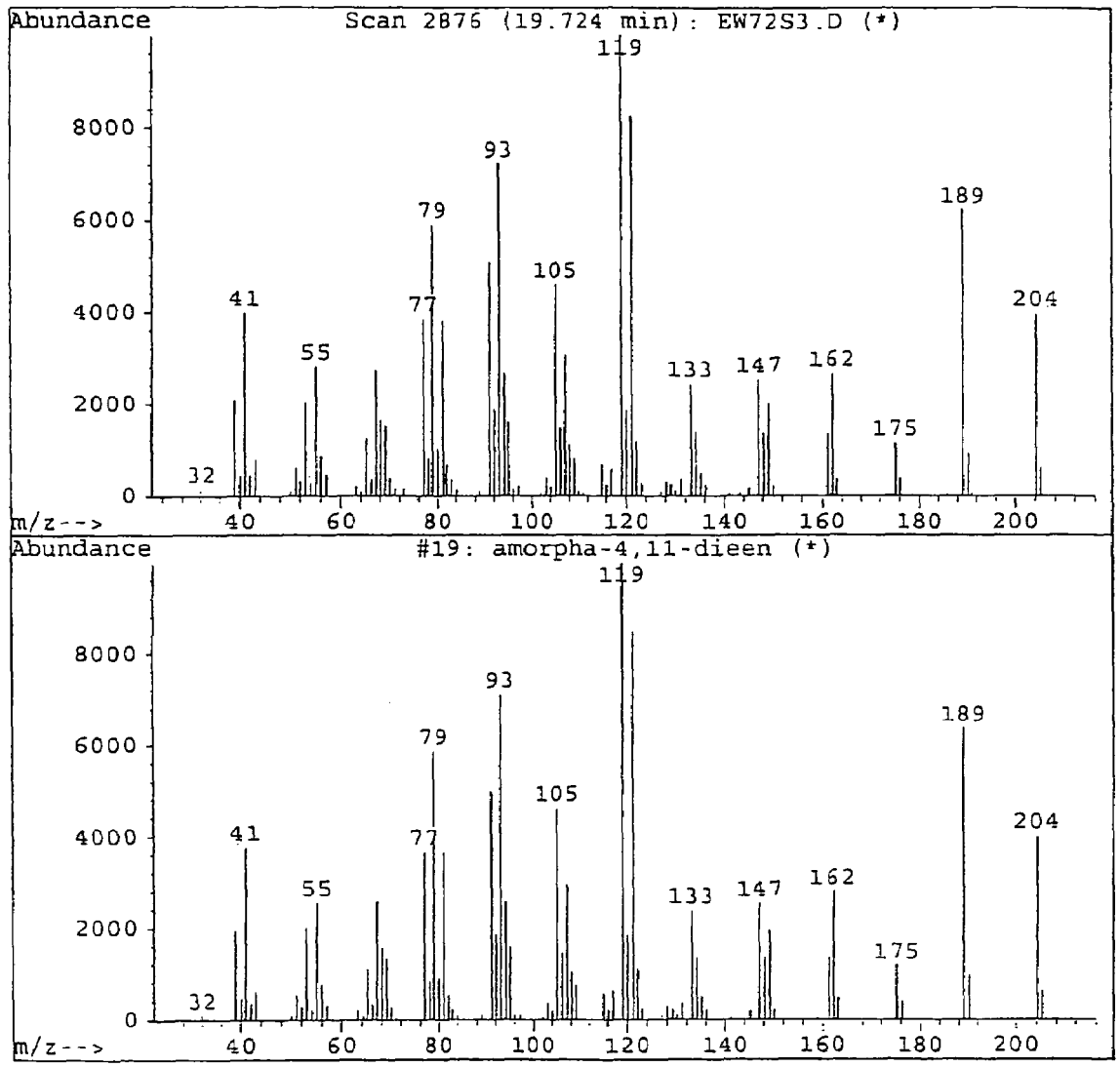

FIG. 6: Mass spectrum of reference amorphadiene compared with mass spectrum of the FPP assay with terpene cyclases (synthases) purified from *A.annua*. This comparison yielded a quality score of 99%, corresponding with a maximum score of identicalness.

Figure 7:
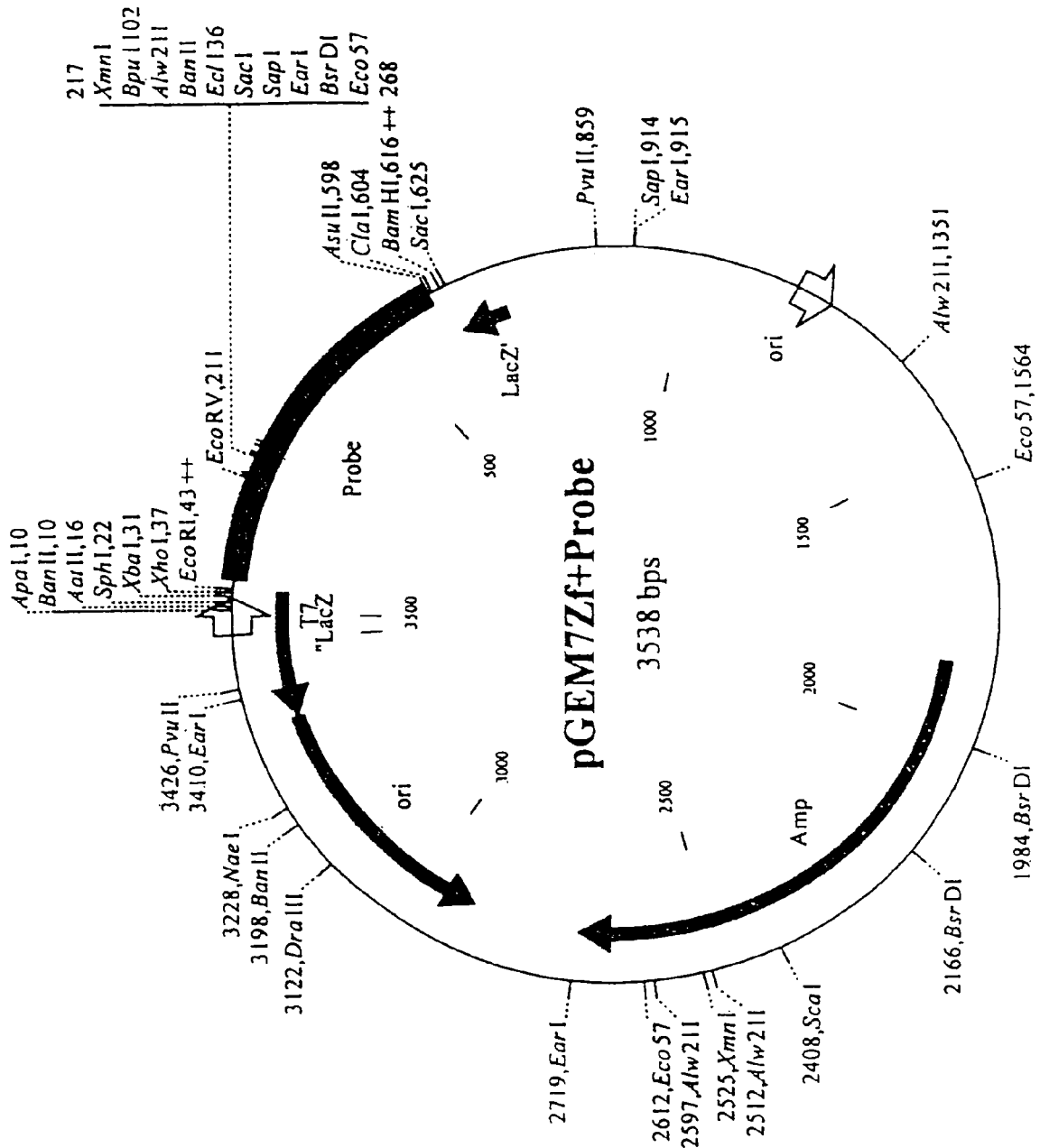

FIG. 7: Probe generated by PCR and cloned into PGEM 7Zf$^+$.

FIG. 8: Nucleotide sequence and deduced amino acid sequence of the probe (538 bp) generated by PCR with primers A and B.

Figure 9:
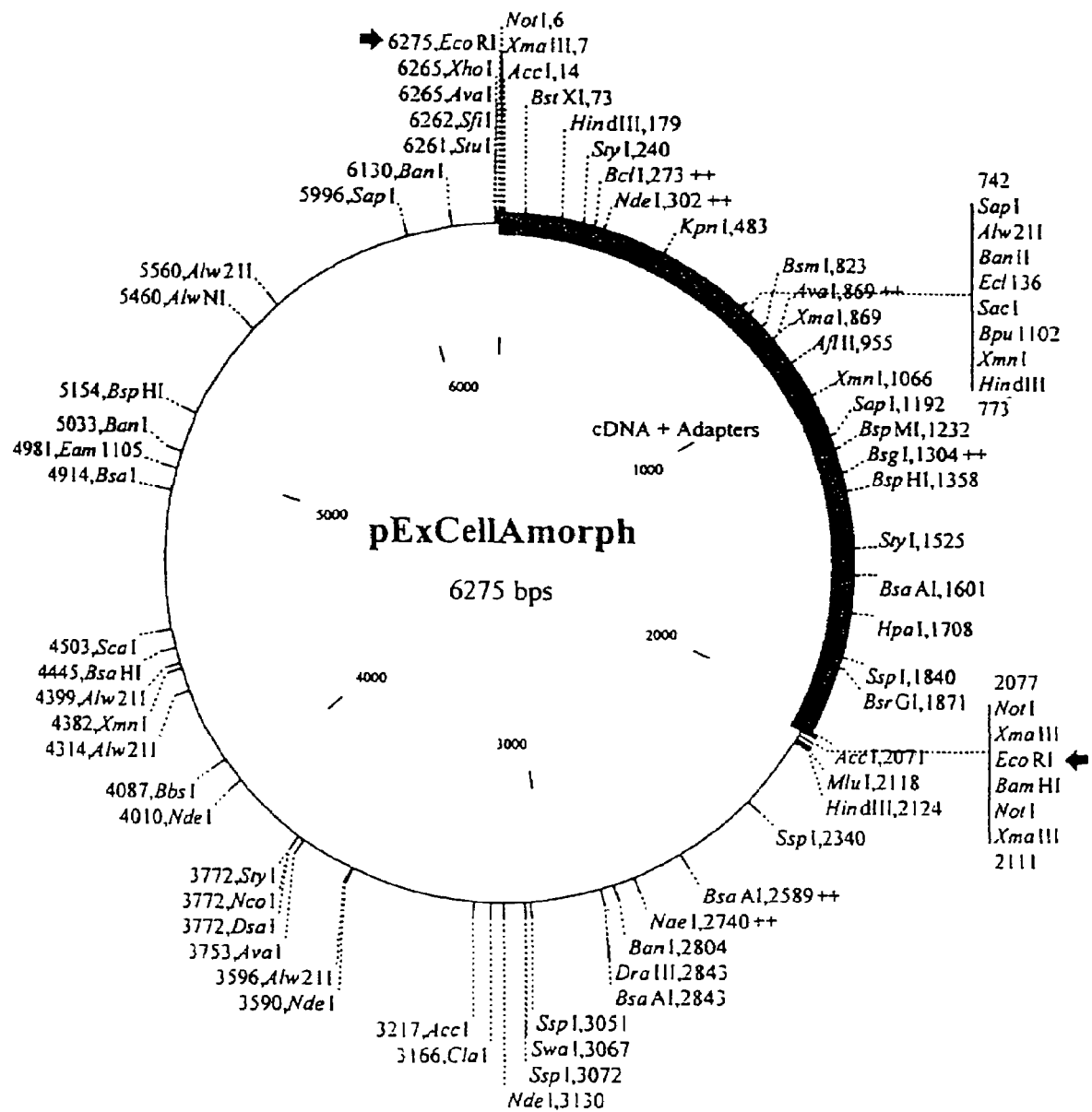

FIG. 9: Released plasmid of a positive clone isolated from the cDNA library of induced *A.annua*.

FIG. 10: Nucleotide sequence and deduced amino acid sequence of a positive clone (amorphadiene synthase encoding gene) isolated from the cDNA library of induced *A.annua*. The sequence is flanked with EcoRI (NotI) adapters (Gibco BRL).

Figure 11:
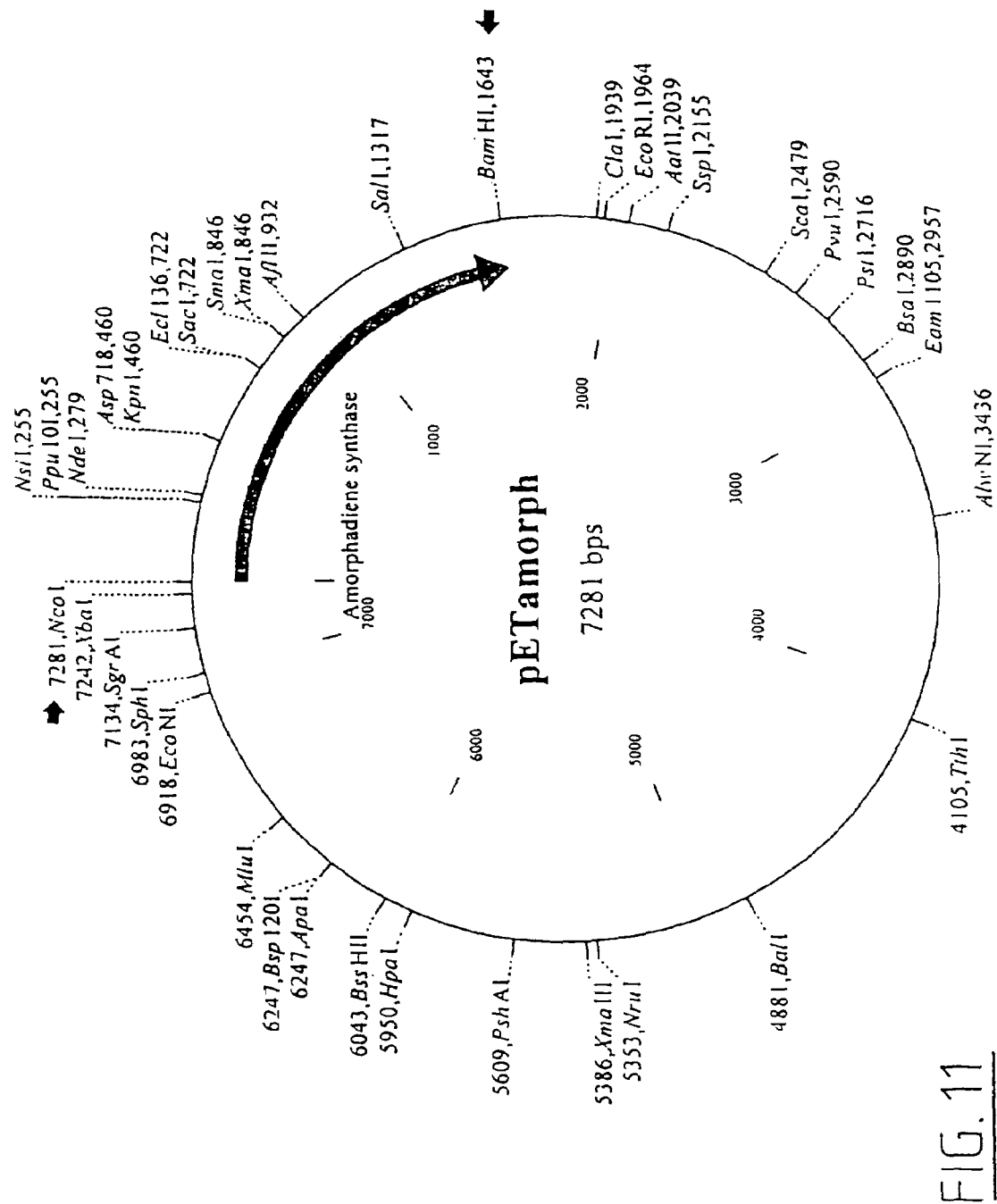

FIG. 11: Part, between start and stop codon (flanked by NcoI and BamHI sites, respectively), of the amorphadiene synthase encoding gene cloned in the NcoI/BamHI site of the expression vector pET 11d.

FIG. 12: Nucleotide sequence and deduced amino acid sequence of the amorphadiene synthase encoding gene, between start and stop codon (flanked by NcoI and BamHI sites, respectively), obtained by PCR with primers C and D.

Figure 13:
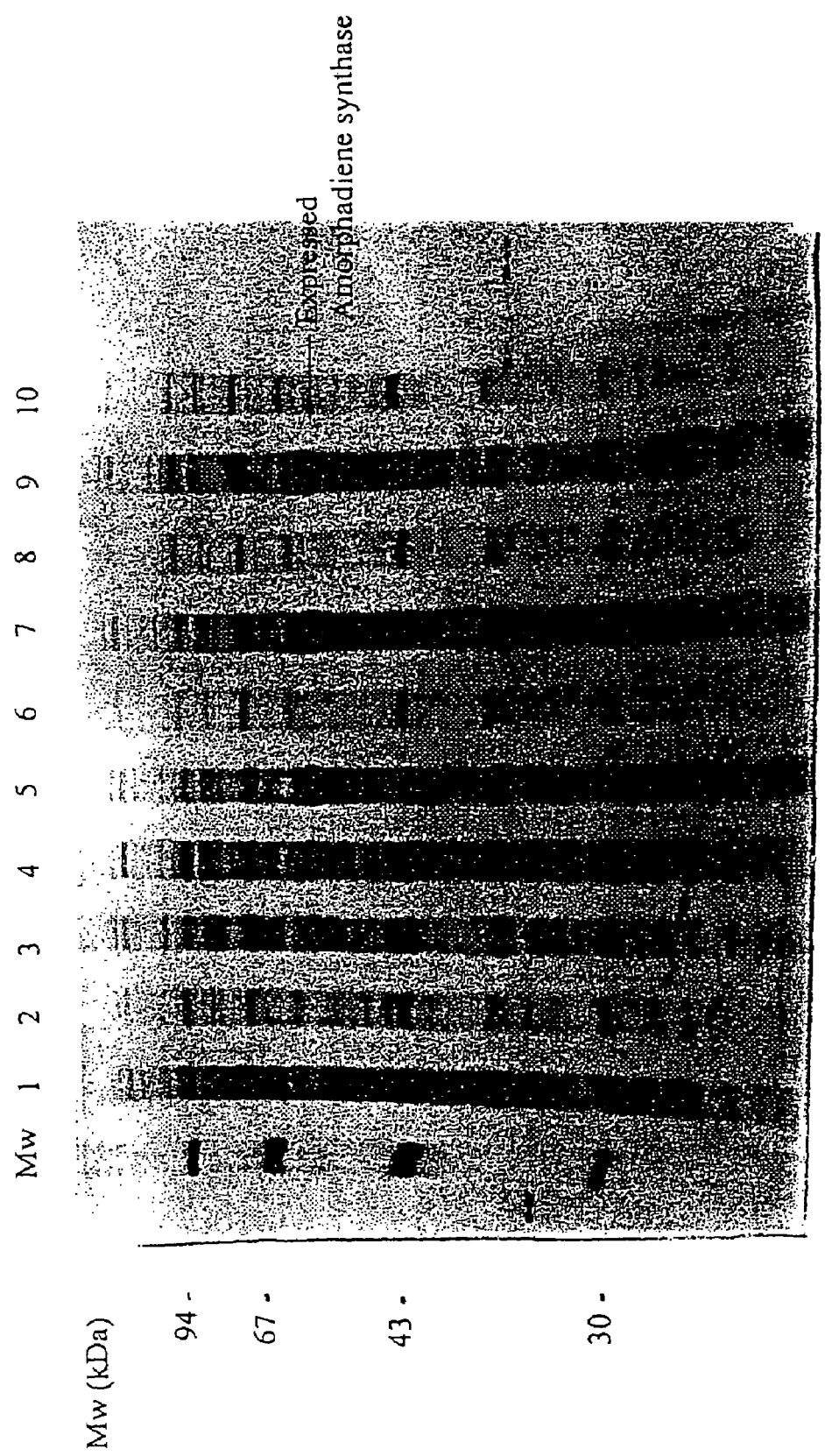

FIG. 13: SDS-PAGE gel: lanes 1 and 2 show pellet and supernatant of pET 11d, respectively (negative control); lanes 3 and 4 show pellet and supernatant of tobacco 5-epi-aristolochene synthase (TEAS) gene in pET 11d (positive control), lanes 5, 7, 9 and 6, 8, 10, respectively show pellet and supernatant of amorphadiene synthase in pET 11d. All constructs were expressed in *E.coli* BL21 (DE3). The lanes with the pellet fractions of TEAS in pET 11d (positive controls) and amorphadiene synthase in pET 1id show a clear spot which was not present in the negative control pET 11d. Mw is low Molecular Weight marker (Pharmacia Biotech).

Figure 14:
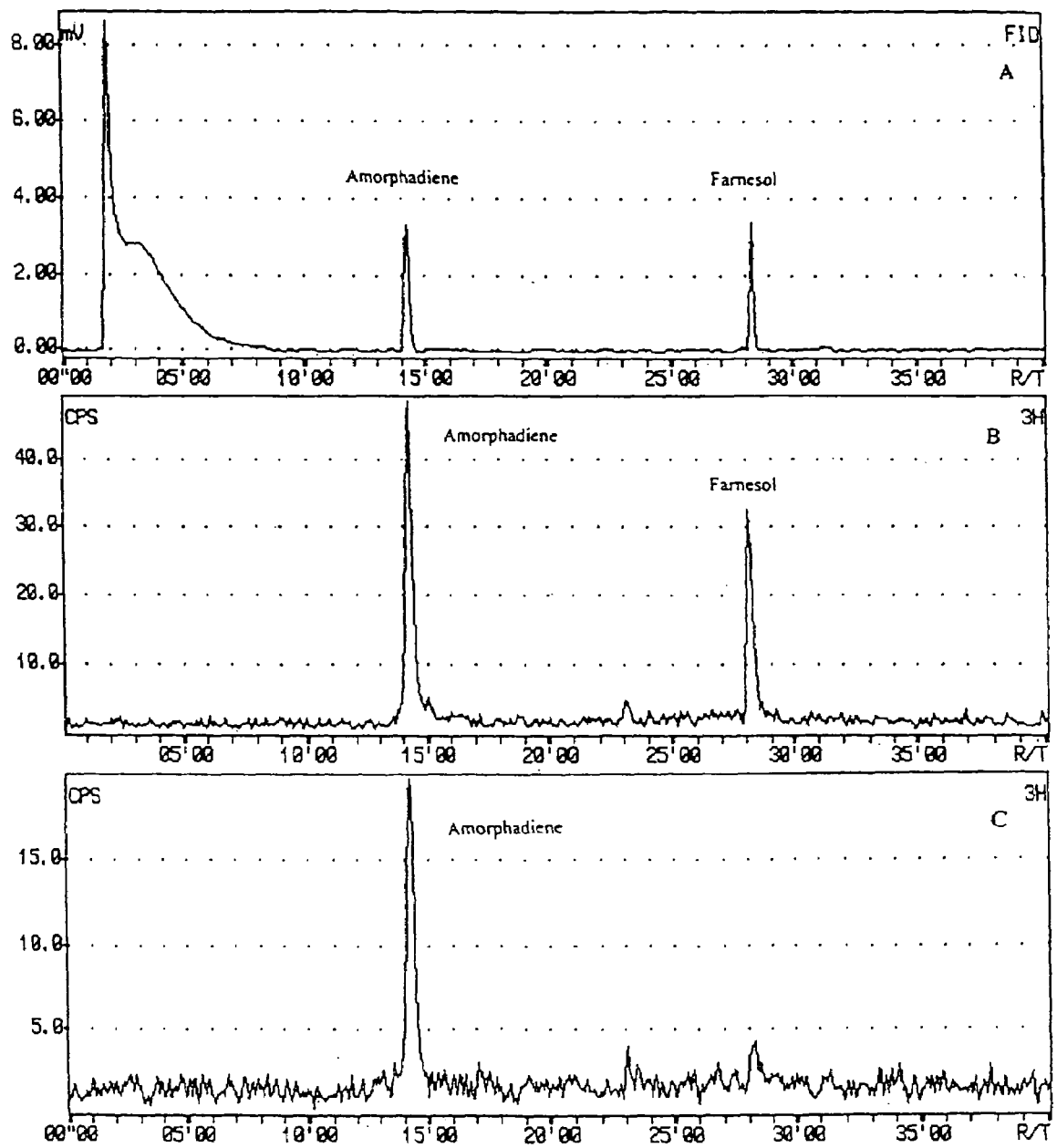

FIG. 14: A. Flame Ionization Detector (FID) signals of amorpha-4,11-diene and farnesol (references); B. Radio-GC chromatograms of the [$^3$H]-FPP-assays with intact BL21 (DE3) cells, transformed with the amorphadiene synthase encoding gene in the expression vector pET 11d; C. Radio-GC chromatograms of the [$^3$H]-FPP-assays with the supernatant of sonicated BL21 (DE3) cells, transformed with the amorphadiene synthase encoding gene in the expression vector pET 11d.

Figure 15:
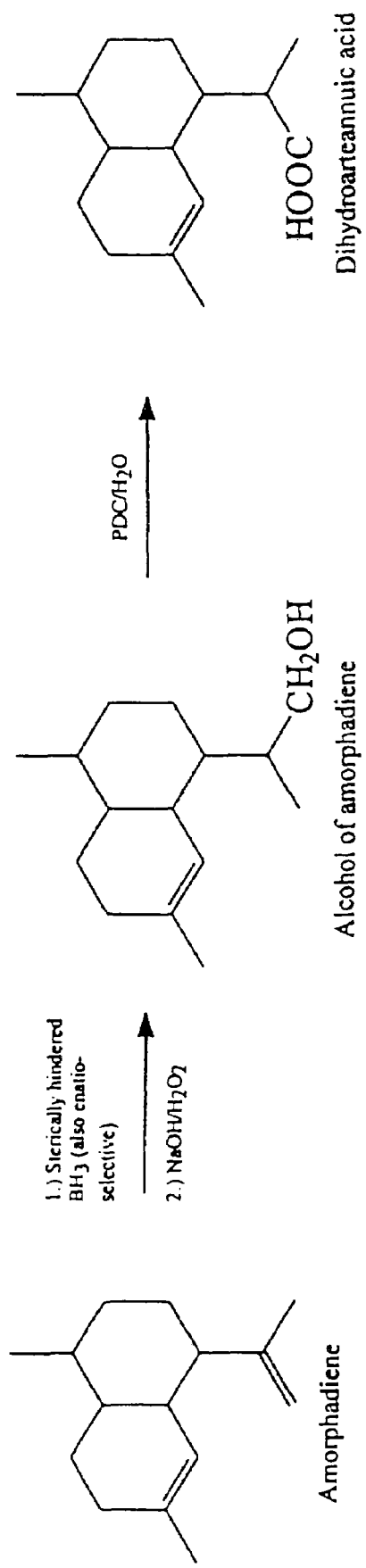

FIG. 15: Hypothetical chemical synthesis of dihydroarteannuic acid using amorpha-4,11-diene as a precursor. The reaction consists of an enantio-, stereo- and region selective (anti-markownikoff) hydroboration of amorphadiene with BH$_3$ followed by an oxidation of the formed trialkylboranes with NaOH/H$_2$O$_2$ yielding the alcohol. A mild oxidation of the alcohol to the acid can be obtained with PDC (pyridinium dichromate) without attacking the second double bond.

Figure 16:
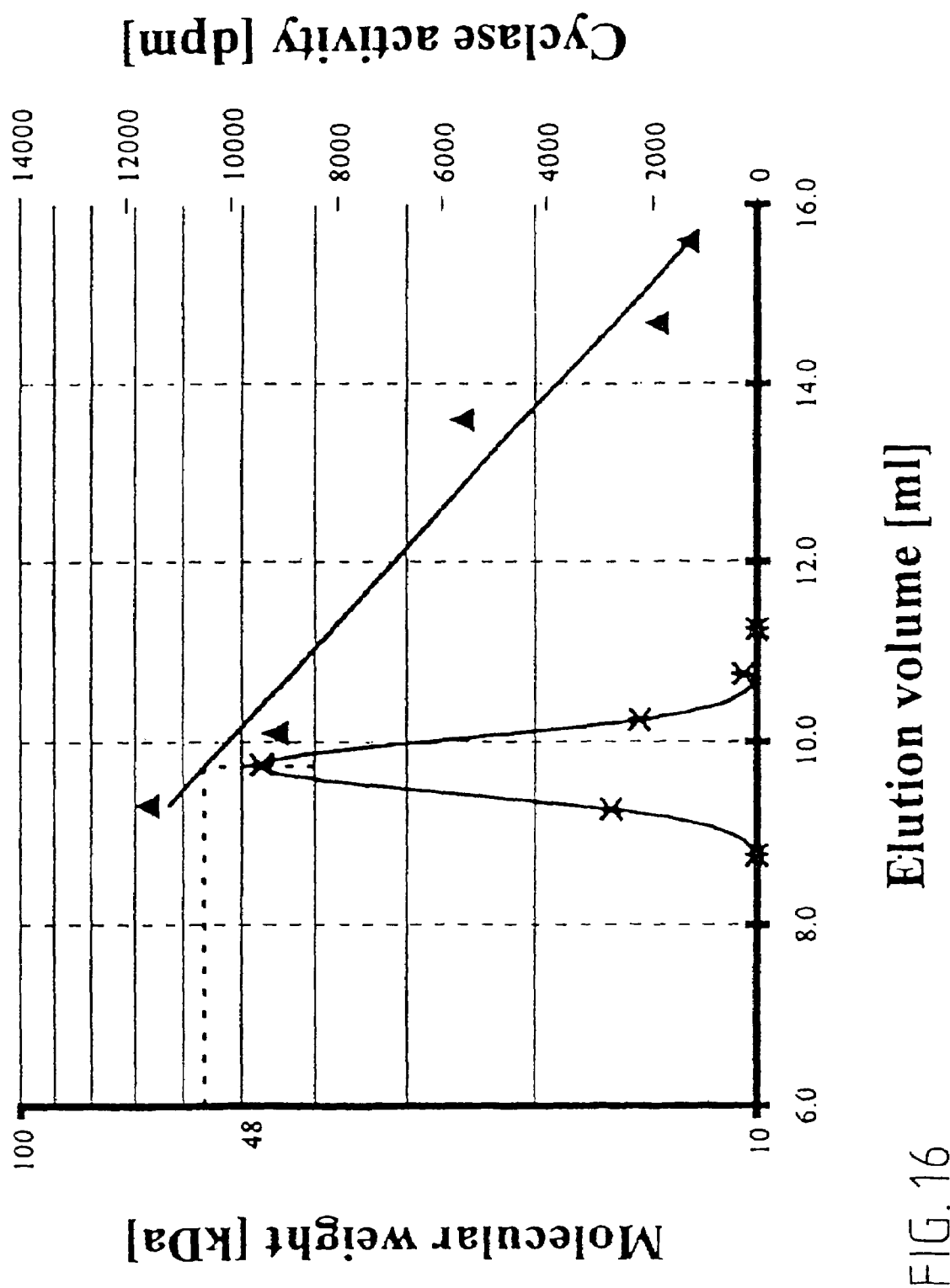

FIG. 16: Determination of the molecular weight of amorpha-4,11-diene synthase by size-exclusion chromatography (gel filtration). -*- is activity curve; -▼- is molecular weight markers; - is molecular weight calibration line.

EXAMPLES

Example 1

Conversion of Farnesyl Pyrophosphate into Amorphadiene by Amorphadiene Synthase

A. Isolation, Partial Purification and Identification of Amorphadiene Synthase from *A.annua*

During enzyme isolation and preparation of the assays, all operations were carried out on ice or at 4° C. Ten grams of frozen young leaves from greenhouse-grown *A.annua* were ground in a pre-chilled mortar and pestle in 40 ml of pre-chilled buffer containing 25 mM MES (pH 5.5), 20% (v/v) glycerol, 25 mM sodium ascorbate, 25 mM NaHSO$_3$, 10 mM MgCl$_2$ and 5 mM DTT (buffer A) slurried with 1 g polyvinylpolypyrrolidone (PVPP) and a spatula tip of purified sea sand. Ten grams of polystyrene resin (Amberlite XAD-4, Serva) were added and the slurry was stirred carefully for 10 min and then filtered through cheesecloth. The filtrate was centrifuged at 20,000 g for 20 min (pellet discarded), and then at 100,000 g for 90 min. A 3-ml subsample of the supernatant was desalted to a buffer containing 15 mM MOPSO (pH 7.0), 10% (v/v) glycerol, 1 mM sodium ascorbate, 10 mM MgCl$_2$ and 2 mM DTT (buffer B) and used for enzyme assays/product identification (see below at 'B').

The remainder of the supernatant was added to 12.5 g DEAE anion exchanger (Whatman DE-52), which had been rinsed several times with buffer A, and stirred carefully for 10 min. After centrifugation at 18,000 g for 20 min, the supernatant was decanted and the DE-52 pellet discarded. Proteins in the supernatant were precipitated by adding (NH$_4$)$_2$SO$_4$ to a final concentration of 70%, careful stirring for 30 min, and centrifugation at 20,000 g for 10 min. The resulting pellet was resuspended in 6 ml buffer A and desalted to buffer B. After addition of glycerol up to 30% (v/v) this enzyme preparation could be frozen in liquid $N_2$ and stored at −80° C. without loss of activity. 0.5 ml of this enzyme preparation was applied to a Mono-Q FPLC column (HR5/5, Pharmacia Biotech), previously equilibrated with buffer B without sodium ascorbate, with 0.1 Tween-20. The enzyme was eluted with a gradient of 0-2.0 M KCl in the same buffer. For determination of enzyme activities, 50 µl of the 0.75-ml fractions were diluted 2-fold in an Eppendorf tube with buffer B and 20 µM [$^3$H]FPP was added. The reaction mixture was overlaid with 1 ml of hexane to trap volatile products and the contents mixed. After incubation for 30 min at 30° C., the vials were vigorously mixed, and centrifuged briefly to separate phases. A portion of the hexane phase (750 µl) was transferred to a new Eppendorf tube containing 40 mg of silica gel (0.035-0.07 mm, pore diameter 6 nm, Janssen Chimica) to bind terpenols produced by phosphohydrolases, and, after mixing and centrifugation, 500 µl of the hexane layer was removed for liquid scintillation counting in 4.5 ml of Ultima Gold cocktail (Packard). The active fractions were combined, and an assay carried out to determine product identity (see below). After the Mono-Q step, the enzyme was separated from all other FPP-converting activities (FIG. 5C). This enzyme preparation was used for the measurement of enzyme characteristics such as molecular weight and $K_m$. The molecular weight was determined using size-exclusion chromatography. 200 µl of the Mono-Q eluent was loaded on a Superdex 75 (H/R10/30, Pharmacia Biotech) and eluted in the same buffer as used for Mono-Q. Enzyme activities in 0.5 ml fractions were determined as described for Mono-Q, but using undiluted eluent. The column was calibrated using cytochrome C, ribonuclease A, α-chymotrypsinogen, ovalbumin and BSA (all from Sigma) The estimated molecular weight was 56 kDa (FIG. 16). Enzyme-kinetics were determined using 5- and 10-fold diluted Mono-Q eluted enzyme preparation and [$^3$H]-FPP concentrations ranging from 0.25-100 µM. $K_m$ for amorphadiene synthase was 0.6 µM.

B. Determination of Product Identity

For determination of product identity, 20 µM [$^3$H]-FPP (Amersham; for radio-GC analysis) or 50 µM unlabelled-FPP (Sigma; for GC-MS analysis) were added to 1 ml of the enzyme preparations. After the addition of a 1 ml redistilled pentane overlay to trap volatile products, the tubes were carefully mixed and incubated for 1 h at 30° C. Boiled samples were used as controls. Following the assay, the tubes were vigorously mixed. The organic layer was removed and passed over a short column of aluminum oxide overlaid with anhydrous $MgSO_4$. The assay was extracted with another 1 ml of diethyl ether which was also passed over the aluminum oxide column, and the column washed with 1.5 ml of diethyl-ether. For GC-analysis, the combined pentane/diethyl-ether mixture was slowly concentrated under a stream of $N_2$.

Radio-GLC was performed on a Carlo-Erba 4160 Series gas chromatograph equipped with a RAGA-90 radioactivity detector (Raytest, Straubenhardt, Germany) Sample components eluting from the column were quantitatively reduced before radioactivity measurement by passage through a conversion reactor filled with platinum chips at 800° C. Samples of 1 µl were injected in the cold on-column mode. The column was a fused silica capillary (30 m×0.32 mm i.d.) coated with a film of 0.25 µm of polyethylene glycol (EconoCap EC-WAX, Alltech Associates) and operated with a He-flow of 1.2 ml min$^{-1}$. The oven temperature was programmed to 70° C. for 5 min, followed by a ramp of 5° min$^{-1}$ to 210° C. and a final time of 5 min. To determine retention times and peak identities (by co-elution of radioactivity with reference standards), about 20% of the column effluent was split with an adjustable splitter to an FID (temperature 270° C.). The remainder was directed to the conversion reactor and radio detector. $H_2$ was added prior to the reactor at 3 ml min$^{-1}$, and $CH_4$ as a quench gas prior to the radioactivity detector (5 ml counting tube) to give a total flow of 36 ml min$^{-1}$. The major [$^3$H]-labeled product co-eluted with the amorphadiene reference standard (retention time 14 min) (FIG. 5B). The second radiolabeled product is farnesol, the product of aspecific phosphohydrolase activity. After the Mono-Q step, the enzyme was separated from all other FPP-converting activities (FIG. 5C). This enzyme-preparation was used for the measurement of enzyme characteristics such as molecular weight and $K_m$.

GC-MS analysis was performed using a HP 5890 series II GC and HP 5972A Mass Selective Detector (Hewlett-Packard) equipped with an HP-SMS or HP-Innowax column (both 30 m×0.25 mm i.d., 0.25 µm df). The oven was programmed at an initial temperature of 70° C. for 1 min, with a ramp of 5° C. min$^{-1}$, to 210° C. and final time of 5 min. The injection port (splitless mode), interface and MS source temperatures were 175, 290 and 180° C., respectively, and the He inlet pressure was controlled by electronic pressure control to achieve a constant column flow of 1.0 ml min$^{-1}$. Ionization potential was set at 70 eV, and scanning was performed from 30-250 amu. The $(NH_4)_2SO_4$ precipitated enzyme preparation was free of endogenous sesquiterpenes. GC-MS analysis on the two different GC-columns of sesquiterpene products generated from FPP by this enzyme preparation showed that the main product had a mass spectrum and retention time equal to that of the semi-synthetically produced amorphadiene (FIG. 6).

Example 2

Isolation and Characterization of the Amorphadiene Synthase Encoding Gene

A. Induction of Transcription

As revealed in part III of FIG. 2, DHAA is photo-oxidatively converted into DHAA-OOH. In this reaction a reactive form of oxygen (singlet $O_2$) is added to DHAA. DHAA plays the role of an anti-oxidant, a scavenger of reactive oxygen species. Artemisinin is the stable end product of this reaction in which reactive oxygen is stored. Under stress conditions, (for example photo-stress, frost, drought or mechanical damage) reactive species of oxygen are formed in the plant. In response to this reactive oxygen generally plants are producing anti-oxidants. It is likely that *A.annua* will produce DHAA as anti-oxidant in response to this release of reactive oxygen. By exposing *A.annua* to stress conditions the transcription of the gene encoding amorphadiene synthase will be induced. To achieve this situation *A.annua* plants grown under climate room conditions (23° C., 90% moisture, 3000 lux) were exposed to stress conditions by putting them for one hour at approximately 30% moisture (drought stress) and 6000 lux (photo stress) at 30° C.

B. Isolation of Total RNA

Total RNA of stress induced plants (according to example 2.A) was isolated from young leaves by the method of Verwoerd et al. (Nucleic Acids Research 17(6), 2362 (1989)). DNase I (Deoxyribonuclease I, RNase free) was used to remove DNA from the RNA isolate. The DNase I was inactivated by exposure at 70° C. during 15 minutes.

C. cDNA Synthesis

The reverse transcription reaction was carried out in a 20 μl reaction containing 5 μg total RNA, 0.2 μg oligo (dT)$_{12}$, 0.5 mM each dATP, dTTP, dCTP and dGTP, 10 mM DTT, 2 U ribonuclease inhibitor (Gibco BRL), first strand synthesis buffer (Promega) and catalyzed with 200 U Moloney murine leukemia virus (M-MLV) reverse transcriptase RNase H minus (Promega). After 1 h incubation at 37° C. the reaction was stopped by storing the reaction mixture at −20° C.

D. PCR-based Probe Generation

Based on comparison of sequences of terpenoid synthases, two degenerated primers were designed for two conserved regions. The sequence of the sense primer (primer A) was 5'-GA(C/T) GA(G/A) AA(C/T) GGI AA(G/A) TT(C/T) AA(G/A) GA-3' and the sequence of the anti sense primer (primer B) was 5'-CC (G/A)TA IGC (G/A)TC (G/A)AA IGT (G/A)TC (G/A)TC-3'. PCR was performed in a total volume of 100 μl containing 0.5 μM of each of these two primers, 0.2 mM each DNTP, 1 U Super Taq polymerase/1×PCR buffer (HT Biotechnology LTD, Cambridge, England) and 2 μl cDNA. The reaction was incubated in a thermocycler (PTC 150, MJ-research) with 1 minute denaturation at 95° C., 1 minute annealing at 40° C. and 1 minute and 15 seconds elongation at 72° C. during 40 cycles. Agarose gel electrophoresis revealed a single specific PCR product of approximately 550 bp (538 bp). Such a specific amplification product was only obtained when using cDNA made of RNA isolated from stress induced plants. The PCR product was made blunt by using DNA polymerase I large fragment (Klenow), gel-purified and subcloned in Sma I digested pGEM 7Zf(+) (Stratagene) (FIG. 7) and *E.coli* DH5α (Gibco BRL) was transformed with this construct. The inserts of 8 individual transformants were sequenced and they all had the same sequence as shown in FIG. 8.

E. cDNA Library Construction

Synthesis of the second strand of the cDNA was done analogous to the RiboClone® cDNA synthesis System (Promega). After ligation with EcoR I (Not I) adapters (Gibco BRL) with sequence:

```
5'-pGTCGACGCGGCCGCG-3'

3'-CAGCTGCGCCGGCGCTTAA-OH-5'
``` the double stranded DNA was ligated into λ ExCell EcoRI/CIP (Pharmacia Biotech). For packaging and plating of the cDNA library, the Ready-To-Go® Lambda Packaging Kit (Pharmacia Biotech) was used. The titer of the unamplified library was 1.2×10$^6$ plaque forming units.

F. Library Screening

For library screening 200 ng of the PCR amplified probe (FIG. 8) was gel purified, randomly. labeled with [α-$^{32}$P] dCTP, according to the manufacturer's recommendation (Random Primed DNA Labeling Kit, Boehringer Mannheim Biochemica) and used to screen replica filters of 10$^4$ plaques of the cDNA library plated on *E.coli* NM 522. The hybridization was performed for 16 h at 68° C. in 1 M NaCl, 1% SDS and 10% PEG (5000-7000). Filters were washed two times for 10 minutes at 50° C. in 2×SSC with 0.1% SDS and exposed for 16 h to a Fuji X-ray film at −70° C. Clones yielding positive signals were isolated through a second and third round of hybridization. By transfecting *E.coli* NP66 (Pharmacia Biotech) with the positive clones, plasmid releases (FIG. 9) were obtained according to the manufacturer's instructions (Pharmacia Biotech). Sequencing of these positive clones yielded a sequence as revealed in FIG. 10.

Example 3

Expression of the Amorphadiene Synthase Encoding Gene in *E.coli* BL21 (DE3)

For functional expression the cDNA clone was subcloned in frame into the expression vector pET 11d (Stratagene). To introduce suitable restriction sites for subcloning, the gene was amplified by PCR using a sense primer (primer C) 5'-GTCGACAAA<u>CCATGG</u>CACTTACAGAA G-3' (introducing a NcoI site at the start codon ATG) and an anti-sense primer (primer D): 5'-GGAT<u>GGATCC</u>TCATATACTCATAGGATAAACG-3' (introducing a BamHI site directly behind the stop codon TGA). The PCR reaction was performed under standard conditions. After digestion with BamHI and NcoI, the PCR product (FIG. 12) and the expression vector pET 11d were gel purified and ligated together to yield a construct as revealed in FIG. 11.

To obtain expression, this gene construct (FIG. 11), pET 11d without an insert as negative control, and pET 11d with the tobacco 5-epi-aristolochene synthase (TEAS) gene (Back et al., Archives of Biochemistry and Biophysics 315(2) 527-532 (1994); Facchini & Chappell, Proc. Natl. Acad. Sci. USA 89, 11088-11092 (1992); Back & Chappell, The Journal of Biological Chemistry 270, 7375-7381 (1995)) as positive control were transformed to *E.coli* BL21 (DE3) (Stratagene), and grown overnight on LB agar plates supplemented with ampicillin at 37° C. Cultures of 50 ml LB medium supplemented with ampicillin (100 μg/ml) and 0.25 mM isopropyl-1-thio-β-D-galactopyranoside (IPTG) were inoculated with these over night cultures to A$_{600}$=0.5 and grown for 3 h at 27° C. The cells were harvested by centrifugation during 8 minutes at 2000 g and resuspended in 2 ml assay buffer. An aliquot of 1 ml resuspended cells was sonicated on ice four times for 5 seconds with 30 second intervals, centrifuged for 5 minutes at 4° C. in a microfuge (13.000 rpm) and the supernatant used for cyclase enzyme activity determinations and SDS-PAGE gel electrophoresis.

Expression of the amorphadiene synthase gene-pET 11d construct (FIG. 11) in *E.coli* BL21 (DE3) yielded a protein of approximately 50 to 60 kDa as shown in FIG. 13 lane 5 to 10. This agrees well to the size of amorphadiene synthase isolated from *A.annua*, which was determined to be 56 kDa (FIG. 16).

Example 4

Conversion of FPP into Amorthadiene by Amorphadiene Synthase Expressed in *E.coli*

Besides the supernatant of sonicated cells, also intact cells were used in the FPP assay. The FPP assay, GC-RAGA and GC-MS analyses were performed as described previously. FIGS. 14 and 14A are revealing the GC-RAGA chromatograms of the assays with intact transformed cells and with the supernatant of sonicated transformed cells, respectively. In both assays amorphadiene was produced. Identification of these assay products with the GC-MS gave a mass-spectrum identical to the mass-spectrum of the reference amorphadiene with a quality score of 99% (maximum score), mass spectra were identical to the spectra as shown in FIG. 6. No amorphadiene was found in assays done with the positive and negative controls.

Example 5

Expression of amorpha-4,11-diene Synthase in Transgenic Tobacco

There are many ways to introduce DNA into a plant cell. Suitable methods by which DNA can be introduced into the plant cell include *Agrobacterium* infection or direct delivery of DNA such as, for example, by PEG-mediated transformation of protoplasts (Omirulleh et al., Plant Molecular Biology 21, 415-428 (1993)) or electroporation, by acceleration of DNA coated microprojectiles (for example, microprojectile bombardment) microinjection, etc.

Because *Agrobacterium tumefaciens*-mediated transformation of *Artemisia annua* and *Nicotiana tabacum* with a sesquiterpene cyclase gene is known in literature (Vergauwe et al., Plant Cell Reports 15, 929-933 (1996); Hohn and Ohlrogge, Plant Physiol. 97, 460-462 (1991)) delivery of expression units (cassettes), containing the amorphadiene synthase encoding gene, mediated by *Acrobacterium* seemed to be a rational approach.

There are several binary vector systems suitable to transfer the amorphadiene synthase encoding gene assembled in an expression cassette behind a suitable promoter (for example, the cauliflower mosaic virus (CaMV) 35S promoter) and upstream of a suitable terminator (for example, the nopaline synthase transcription terminator (nos-tail)) to tobacco and/or *A.annua*.

Analogous to EXAMPLE 3, suitable restriction sites for subcloning were introduced by using PCR with a sense primer (primer G) 5'-GA GGATCC ATG TCA CTT ACA GAA-3' introducing a BamHI site preceding the start codon ATG) and an anti-sense primer (primer H) 5'-AT GGATCC TCA TAT ACT CAT AGG A-3' (introducing a BamHI site directly behind the stop codon TGA). After digestion with BamHI the PCR product and the plant-expression cassette pLV399 were gel purified and ligated to provide the gene encoding amorpha-4,11-diene synthase with the cauliflower mosaic virus 35S promoter and a nopaline synthase transcription terminator. The plant-expression casette pLV399 is a pUC 19 vector (Yanisch-Perron, C. et al., Gene 33, 103-119 (1985)) in which the multiple cloning site (polylinker) is replaced by a CaMV 35 S promoter BamHI fused to a nos-tail (terminator) flanked by the 'unique' sites; EcoRI, KpnI, XhoI, and a HindIII site downstream from the promoter and EcoRI, XhoI, PstI, SphI, KpnI, HindIII upstream from the terminator. The orientation of the amorpha-4,11-diene encoding gene in pLV399 was checked by restriction analysis with PstI and NdeI. After partial digestion of this construct with KpnI the amorpha-4,11-diene encoding gene flanked by the 35S promotor and nos terminator was ligated into the KpnI digested binary vector pCGN1548.

To mobilize the recombinant binary vector to *Agrobacterium tumefaciens* LBA4404 (Gibco BRL, Life Technologies), a triparental mating procedure was carried out by using *E.coli* (DH5α) carrying the recombinant binary vector and a helper *E.coli* carrying the plasmid pRK2013 to mobilize the recombinant binary vector to *A. tumefaciens* LBA4404.

This transformed *Aqrobacterium* strain was used for transformation of explants from the target plant species. Only the transformed tissue carrying a resistance marker (kanamycin-resistance, present between the binary plasmid T-DNA borders) regenerated on a selectable (kanamycin containing) regeneration medium. (According to Rogers S G, Horsch R B, Fraley R T Methods Enzymol (1986)118: 627-640).

The plants regenerated out of the transformed tissue expressed the amorphadiene synthase gene as followed from the presence therein of amorphadiene as confirmed by GC-MS analyses.

Example 6

Conversion of Amorphadiene into Artemisinin (DHA) by *A.annua*

This assay was carried out in a way analogous to the method as described by Koepp et al. (The Journal of Biological Chemistry 270, 8686-8690 (1995)). Radioactive ($^3$H-labeled) amorphadiene was fed to leaf discs of *A.annua*. For the infiltration of amorphadiene into the leaf discs of *A.annua* the radioactive amorphadiene can be made water soluble by complexation with cyclodextrins, for example. Radioactive amorphadiene is obtained by using the FPP-assay with the transformed *E.coli* BL21 (DE3) cells (carrying the cloned amorphadiene synthetase gene of *A.annua*). Identification of the product(s) made in this assay was done by radio-GC analysis. The expected intermediates arteannuic acid (AA), dihydroarteannuic acid (DHAA) and the end product artemisinin were all used as references.

A mixture of α-cyclodextrin, β-cyclodextrin, γ-cyclodextrin, and partially $^3$H-labeled amorpha-4,11-diene (20 μM) in a molar ratio of 5:5:5:1 was prepared and *A.annua* leaf discs were incubated in this mixture. After 120 hours of incubation artemisinic acid and dihydroartemisinic acid could be detected by radio-GC in a way analogous to part B of example 1.

Example 7

Expression of amorpha-4,11-diene Synthase in Transgenic *A.annua* and the Production of Artemisinin Transformed *A.annua* plants were prepared as described in example 5.

For the regeneration of *A.annua* the medium for callus, shoot and root induction consisted of Murashige and Skoog micro and macro elements including modified vitamins (Duchefa Biochemie, Haarlem, The Netherlands), 4% (w/v) sucrose, 0.1 mg/L Indole-3-acetic acid (IAA), 0.1 mg/L 6-benzylaminopurine (BAP) and 0.8% (w/v) agar (Plant agar, Duchefa Biochemie, Haarlem, the Netherlands). The pH was adjusted to 5.7 with NaOH prior to the addition of agar. The medium was autoclaved at 1 bar for 20 min. Transformed explants were regenerated on this medium to fully regenerated plants.

The regenerated plants were found to over-express the enzyme amorpha-4,11-diene synthase which led to production of artemisinic acid, dihydroartemisinic acid, and artemisinin at a level above the natural level in non-transformed plants.

Example 8

Expression of the amorpha-4,11-diene Synthase Gene in *Saccharomyces cerevisiae* and *Pichia pastoris*

For functional expression the cDNA clone was subcloned into the inducible expression vector pYES2 (episomal vector, Invitrogen) and the constitutive expression vector (integrating the gene construct into the genome) pGAPZ A (Invitrogen). To introduce suitable restriction sites for subcloning, the gene was amplified by PCR using a sense primer (primer E) 5'-CGA GAATTC ATG TCA CTT ACA G-3' (introducing a EcoRI site preceding the start codon ATG) and an anti-sense primer (primer F) 5'-GGAT CTCGAG TCA TAT ACT CAT-3' (introducing a BamHI site directly behind the stop codon TGA). Subcloning of the PCR product into pYES2 and pGAPZ A was done in a way analogue to Example 3.

The obtained gene constructs were transformed to respectively *Saccharomyces cerevisiae* and *Pichia pastoris* using the *S.cerevisiae* EasyComp™ transformation kit (Invitrogen) to transform *S.cerevisiae* and the *Pichia* EasyComp™ transformation kit (Invitrogen) for transformation of *P.pastoris*. All transformations were carried out according to the instructions of the manufacturer. Growth, selection and induction were also performed in accordance to the instructions of the manufacturer. Harvesting and sonication of the yeast cells was done in an analogous way to the method as described in Example 3.

The FPP assay with the extracts of the yeast cells in which the amorpha-4,11-diene synthase gene was expressed yielded identical GC-RAGA and GC-MS chromatograms as obtained in example 4.

What is claimed is:

1. An isolated DNA sequence encoding a polypeptide having the biological activity of amorpha-4,11-diene synthase, wherein the polypeptide encoded by the DNA sequence has a sequence corresponding to the translation of a DNA sequence exhibiting at least 95% homology to SEQ ID NO: 13.

2. The DNA sequence as claimed in claim 1, wherein the sequence has been isolated from plants producing amorpha-4,11-diene.

3. A method for producing amorphadiene synthase, comprising transforming or transfecting a host cell with the DNA sequence claimed in claim 1.

4. A DNA construct comprising the DNA sequence as claimed in claim 1 operably linked to suitable transcription initiation and termination sequences.

5. A host cell comprising the DNA sequence as claimed in claim 1.

6. The host cell as claimed in claim 5, wherein the cell is a bacterial cell.

7. The host cell as claimed in claim 5, wherein the cell is a plant cell.

8. The host cell as claimed in claim 7, wherein the cell is derived from a plant itself producing sesquiterpenes.

9. The host cell as claimed in claim 5, wherein the cell is a cell selected from an *A. annua* cell, a *V. oblongifolia* cell and an *E. coli* cell.

10. The host cell as claimed in claim 7, wherein the cell is derived from a plant of a genera selected from *Carum, Cichorium, Daucus, Juniperus, Chatnomilla, Lactuca, Pogoslemon* and *Vetiveria*.

11. The plant host cell as claimed in claim 7, wherein the biosynthesis of sesquiterpenes can be elicited in the host cell.

12. The host cell as claimed in claim 7, wherein the cell is derived from a plant of a genera selected from *Capsicum, Gossypium, Lycopersicon, Nicotiana, Phleurn, Solanum* and *Ulmus*.

13. The host cell as claimed in claim 7, wherein the cell is derived from a plant selected from a soybean plant, a sunflower plant and a rapeseed plant.

14. The host cell as claimed in claim 5, wherein the cell is a yeast cell.

15. The host cell as claimed in claim 14, wherein the yeast cell is selected from *Saccharomyces cerevisiae* and *Pichia pastoris*.

16. The host cell as claimed in claim 5, wherein the cell is an oleaginous yeast cell.

17. The host cell as claimed in claim 16, wherein the oleaginous yeast cell is a *Yarrowia lipolytica* cell.

18. The host cell as claimed in claim 5, wherein the cell is part of a tissue or organism.

19. A transgenic plant tissue, comprising at least the host cell as claimed in claim 5.

20. A transgenic plant organism, comprising at least the host cell as claimed in claim 5.

21. A transgenic cell, tissue or transgenic organism harboring in its genome more copies of the DNA sequence as claimed in claim 1 than are present in a corresponding non-transgenic cell, tissue or organism.

22. The transgenic cell as claimed in claim 21, wherein the cell is an *E. coli* cell.

23. The transgenic cell as claimed in claim 21, wherein the cell is a *Saccharoinyces cerevisiae* cell.

24. The transgenic cell as claimed in claim 21, wherein the cell is a *Yarrowia lipolytica* cell.

25. The transgenic organism as claimed in claim 21, wherein the organism is a plant itself producing sesquiterpenes.

26. The transgenic organism as claimed in claim 25, wherein the organism is an organism selected from *A. annua* and *V. oblongifolia*.

27. The transgenic organism as claimed in claim 25, wherein the plant is selected from the genera *Carum, Cichoriuni, Daucus, Juniperus, Charnomilla, Lactuca, Pogostemon* and *Vetiveria*.

28. The transgenic organism as claimed in claim 21, wherein the organism is a plant, and wherein the biosynthesis of sesquiterpenes can be elicited in the host cell.

29. The transgenic organism as claimed in claim 28, wherein the plant is selected from the genera *Capsicum, Gossypium, Lycopersicon, Nicotiana, Phleum, Solanum* and *Ulmus*.

30. The transgenic organism as claimed in claim 21, wherein the organism is a plant selected from soybean, sunflower and rapeseed.

* * * * *

UNITED STATES PATENT AND TRADEMARK OFFICE
CERTIFICATE OF CORRECTION

PATENT NO. : 7,541,172 B2
APPLICATION NO. : 11/488906
DATED : June 2, 2009
INVENTOR(S) : Thorvald Eelco Wallaart and Hendrik Jan Bouwmeester It is certified that error appears in the above-identified patent and that said Letters Patent is hereby corrected as shown below:

In Claim 10, col. 28, line 64, "*Chatnomilla*" should read --*Chamomilla*--.

In Claim 10, col. 28, line 64, "*Pogoslemon*" should read --*Pogostemon*--.

In Claim 12, col. 29, line 3, "*Phleurn*" should read --*Phleum*--.

In Claim 23, col. 30, line 4, "*Saccharoinyces*" should read --*Saccharomyces*--.

In Claim 27, col. 30, lines 14-15, "*Cichoriuni*" should read --*Cichorium*--.

In Claim 27, col. 30, line 15, "*Charnomilla*" should read --*Chamomilla*--.

Signed and Sealed this

Fourth Day of August, 2009

JOHN DOLL
*Acting Director of the United States Patent and Trademark Office*